(12) United States Patent
Provost et al.

(10) Patent No.: US 10,842,894 B1
(45) Date of Patent: Nov. 24, 2020

(54) SYSTEMS AND METHODS FOR TREATING A CONTAMINATED CONTAINER

(71) Applicant: Steribin, LLC, St. George, UT (US)

(72) Inventors: Wayne A. Provost, St. George, UT (US); William J. Christensen, St. George, UT (US)

(*) Notice: Subject to any disclaimer, the term of this patent is extended or adjusted under 35 U.S.C. 154(b) by 0 days.

(21) Appl. No.: 16/795,403

(22) Filed: Feb. 19, 2020

Related U.S. Application Data

(60) Provisional application No. 62/880,520, filed on Jul. 30, 2019.

(51) Int. Cl.
*A61L 2/10* (2006.01)
*A61L 2/26* (2006.01)

(52) U.S. Cl.
CPC .............. *A61L 2/10* (2013.01); *A61L 2/26* (2013.01); *A61L 2202/23* (2013.01)

(58) Field of Classification Search
CPC ........... A61L 2/10; A61L 2/26; A61L 2202/23
See application file for complete search history.

(56) References Cited

U.S. PATENT DOCUMENTS

| | | | | |
|---|---|---|---|---|
| 6,132,784 | A * | 10/2000 | Brandt | A23B 7/015 422/186.3 |
| 6,730,923 | B1 * | 5/2004 | May | A61L 2/10 250/435 |
| 9,125,957 | B2 * | 9/2015 | Freue | C09D 5/14 |
| 2008/0085228 | A1 * | 4/2008 | Yamazaki | A61L 2/20 422/291 |
| 2013/0277574 | A1 * | 10/2013 | Dayton | A61L 2/10 250/455.11 |
| 2015/0298906 | A1 * | 10/2015 | Marastoni | B65B 7/28 414/267 |
| 2017/0028089 | A1 * | 2/2017 | Garrett | A61L 2/0047 |
| 2018/0343898 | A1 * | 12/2018 | Alzeer | A23L 3/28 |

OTHER PUBLICATIONS

TSA, Youtube Video (Year: 2016).*

* cited by examiner

*Primary Examiner* — Sean E Conley
*Assistant Examiner* — Brendan A Hensel
(74) *Attorney, Agent, or Firm* — David R. Conklin; Kirton McConkie

(57) ABSTRACT

A disinfecting device for use in disinfecting a container, wherein the device includes a light source configured to emit an antimicrobial wavelength on one or more surfaces of the container as the container passes through the disinfecting device.

18 Claims, 15 Drawing Sheets

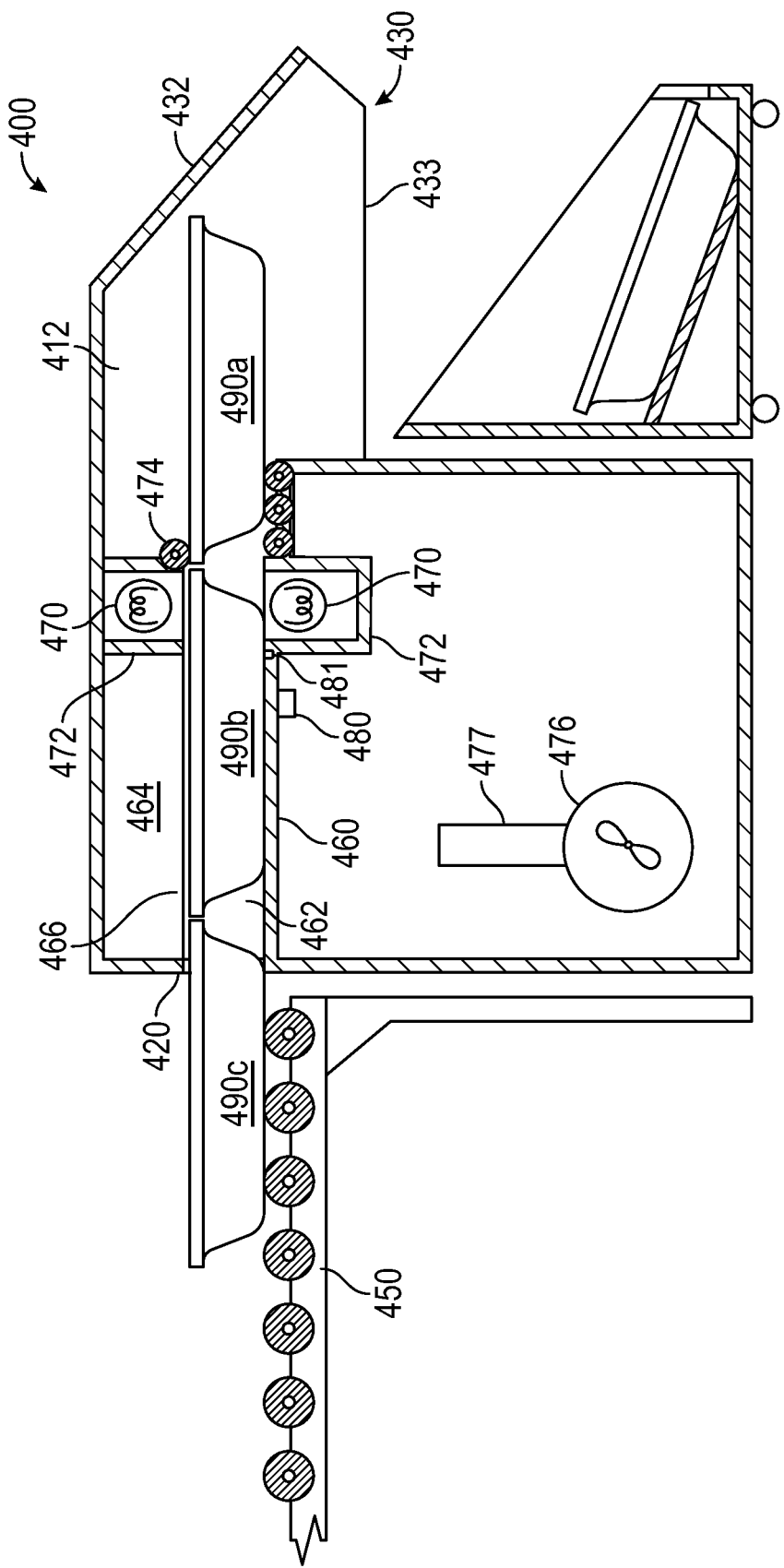

SYSTEMS AND METHODS FOR TREATING A CONTAMINATED CONTAINER

RELATED APPLICATIONS

This application claims priority to U.S. Provisional application Ser. No. 62/880,520 entitled SYSTEMS AND METHODS FOR TREATING A CONTAMINATED SECURITY BIN, filed Jul. 30, 2019, which is incorporated herein in its entirety.

FIELD OF THE INVENTION

The present invention relates generally to a device (herein referred to as a "disinfecting device") for treating a contaminated container. In particular, the present invention relates to a disinfecting device having an enclosed chamber through which a container is passed, wherein the enclosed chamber includes a light source configured to emit an antimicrobial wavelength on one or more surfaces of the container. The present invention further includes systems and methods for treating a contaminated container, wherein the systems and methods utilize a disinfecting device disclosed herein.

BACKGROUND OF THE INVENTION

Infectious diseases commonly spread through the direct transfer of bacteria, viruses or other microbes from contact with contaminated surfaces. Surfaces which are generally understood as having a high likelihood of contamination (i.e., toilets, cutting boards, hands, etc.) or which require high levels of sterility (i.e, surgical instruments, food, etc.) are frequently treated to reduce contamination. These treatments may be as simple as handwashing, or as complex as gamma irradiation. In some instances, a surface may be understood as having a high likelihood of contamination, but the treatment of the surface may be complicated or untreatable due to the material or functional properties of the surface. In some instances, the likelihood of contamination of a surface may be unknown or underappreciated such that the surface is not treated.

For example, more than 2.8 billion people travel by commercial aircraft each year. Travelers often have concerns about the health risks of air travel, including in-flight medical emergencies, exacerbations of chronic medical problems due to changes in air pressure and humidity, barotrauma, relative immobility during flights, close proximity to other passengers with certain communicable diseases, and potential adverse effects of prolonged exposure to recirculated air. In addition to these risks is the underappreciated risk of microbial exposure prior to boarding the plane, namely through contact with contaminated surfaces in the airport.

Bacterial culture tests performed on a variety of airport surfaces revealed high levels of bacteria and viruses on security bins, arm rests, seatbelt buckles, and tray tables. While it is possible to use sanitizer wipes and/or sprays to disinfect arm rests, seatbelt buckles, and tray tables, over time these methods of disinfection produce sticky residues that are not compatible for use with stackable security bins. Accordingly, although methods for disinfecting contaminated airport surfaces exists, challenges still remain. The present invention addresses and overcomes these challenges.

BRIEF SUMMARY OF THE INVENTION

The present invention relates generally to a disinfecting device for treating a contaminated container, including, but not limited to, a security bin for use in an airport. In particular, the present invention relates to a disinfecting device having a housing which encloses a chamber through which a container is passed, wherein the enclosed chamber includes a light source configured to emit an antimicrobial wavelength on one or more surfaces of the container. As used herein, the term "antimicrobial wavelength" is understood to describe any wavelength of light capable of destroying or inhibiting the growth of microorganisms, especially pathogenic microorganisms. The present invention further includes systems and methods for treating a contaminated container, wherein the systems and methods utilize a disinfecting device disclosed herein.

In some instances, a device is provided which is configured to disinfect, sanitize, or otherwise treat and lessen a contaminated condition of one or more surfaces of a container. As used herein, the term "container" is understood to include any object that can be used to hold or transport something. Although the features of the present invention are generally discussed in connection with a security bin container, each feature of each embodiment disclosed herein may be implemented with any container, as defined herein. Further, although generally referred to herein as a "disinfecting device", it is understood that a disinfecting device of the present invention may disinfect, sterilize, sanitize, or otherwise treat and clean one or more surfaces of a contaminated container to achieve a lessened state or condition of contamination. In some instances, a disinfecting device is configured to treat a container to achieve a sterilized condition. In some instances, a disinfecting device is configured to treat a container to achieve a sanitized condition. In some instances, a disinfecting device is configured to treat a container to achieve a disinfected condition.

In some embodiments, a device is provided comprising a housing having a pathway or space into which a container is placed, and/or through which a container is passed, and exposed to an antimicrobial wavelength, wherein the antimicrobial wavelength treats (i.e., disinfects) at least one surface of the container. A device of the present invention may be configured to treat a container temporarily held in a static position, and/or treat a container that is actively moving through the device.

In some instances, a disinfecting device disclosed herein is provided as a standalone unit. In some instances, a disinfecting device disclosed herein is provided as an inline component of a security screening system. In some instances, a disinfecting device disclosed herein is provided as an add-on device or component configured to be combined with or otherwise integrated into an existing component of a security screening system. In some instances, a disinfecting device disclosed herein is provided as an add-on device or component configure to be combined with or otherwise integrated into an existing component of a manufacturing system, an assembly line, a packaging system, or a cleaning system.

In some instances, an enclosed chamber of a disinfecting device disclosed herein comprises a first or upstream opening for receiving a container, an interior through which the container passes, and a second or downstream opening through which the container exits the enclosed chamber. In some instances, the first and second openings comprise a shape and/or dimensions that approximate a cross-sectional shape of a container, but are greater than the actual dimensions of the container to permit passage through the openings. In some instances, the first opening further includes a guide configured to align or otherwise optimize a position of a container prior to entering the device via the first opening.

In some instances, the interior of the enclosed chamber comprises a volume sized to accommodate a single container, wherein the disinfecting device is intended to receive and disinfect only one container at a time. In some instances, the interior of the enclosed chamber comprises a volume sized to accommodate a plurality of containers, wherein the disinfecting device is intended to receive and disinfect one, or one or more containers at a time.

In some instances, at least one of the first and second openings comprises a covering that may be temporarily defeated or bypassed to permit passage of a container. In some instances, the first and second openings include a covering comprising a curtain that is impenetrable or substantially impenetrable to light. In some instances, the first and second openings include a covering comprising a brush seal that is impenetrable or substantially impenetrable to light. In some instance, at least one of the first and second openings comprise a plurality of coverings, wherein the plurality of coverings provide a cumulative effect of containing or substantially containing light within the enclosed chamber of the disinfecting device. In some instances, a covering of at least one of the first and second openings comprise a solid door that is movable between an open and closed position. In some instances, the solid door is moved between the open and closed positions by a motor. In some instances, the solid door is moved between the open and closed positions by force and gravity as a container is moved through the first and/or second openings.

In some instances, a pathway is provided through the enclosed chamber, wherein the pathway interconnects the first and second openings of the disinfection device. In some instances, the pathway is a linear pathway through the enclosed chamber of the disinfecting device. In some instance, the pathway is a nonlinear pathway through the enclosed chamber. In some instances, the pathway comprises a solid surface. In some instances, the pathway comprises an optically clear solid surface. In some instances, at least one surface of the pathway is light scattering. In some instances, the pathway comprises a plurality of rollers which are spaced apart over a length of the pathway.

In some instances, the pathway through the interior of the device is angled or sloped, such that the first opening is positioned at a height that is greater than a height of the second opening. In these instances, a container passes through the interior, along the pathway, under gravitational force. In some instances, a container is physically pushed through the first opening, such as by a user or under the force of an upstream container being driven towards the first opening. Once the container has passed through the first opening, the container slides down the pathway via gravitational force, towards and through the second opening to exit the enclosed chamber.

In some instances, a pathway of the disinfecting device is a level or substantially level pathway through the interior of the device, such that the first and second openings of the device are positioned in a same horizontal plane. In these instances, a container passes through the interior, along the pathway, under a compulsory force. For example, in some instances the pathway further comprises a conveyor belt on which the container rests while passing, or being conveyed, through the interior of the device. In some instances, a container is physically pushed along the pathway, such as by a user or under the force of an upstream container being driven towards or through the first or upstream opening. In some instances, a container is automatically moved through the disinfecting device under a preprogrammed protocol using a systems of motors, controllers, sensors, conveyors, and software for controlling the same.

The enclosed chamber of the present invention further comprises a light source in communication with the interior of the device, such that a container passing through the interior of the enclosed chamber is exposed to an antimicrobial wavelength emitted from the light source. A light source of the present invention may include any type, shape, size, and configuration of light bulb or other form of light source compatible with a disinfecting device disclosed herein. In some instances, a light source further comprises a driver, software and other electrical components adapted to control one or more functions of the light source. In some instances, a light source of the present invention is a pulsed gas discharge lamp configured to emit a high intensity, antimicrobial wavelength of from approximately 1-1000 nm, from 10-121 nm, from 10-200 nm, from 100-400 nm, from 100-280 nm, from 200-280 nm, from 280-315 nm, from 315-400 nm, at a pulse duration of 1-1000 msec, and at an energy of 1-2000 joules/pulse. In some instances, an antimicrobial wavelength is 265 nm. In some instances, a light source is provided configured to emit a pulsed antimicrobial wavelength, wherein the time between two pulses (or voltage signals) is approximately 0.05 seconds, 0.1 seconds, 0.15 seconds, 0.18 seconds, 0.2 seconds, 0.25 seconds, 0.3 seconds, 0.35 seconds, 0.4 seconds, 0.45 seconds, or 0.5 seconds. In some instances, a light source is provided configured to emit a pulsed antimicrobial wavelength at 1 pulse per second, 2 pulses per second, 3 pulses per second, 4 pulses per second, 5 pulses per second, 6 pulses per second, 7 pulses per second, 8 pulses per second, 9 pulses per second, 10 pulses per second, 11 pulses per second, 12 pulses per second, 13 pulses per second, 14 pulses per second, 15 pulses per second, or greater than 15 pulses per second. In some instances, a light source is a UV lamp, including, but not limited to a pulsed UV lamps, a xenon-mercury short-arc lamp, a xenon short-arc lamp, a mercury short-arc lamp, an argon arc lamp, a deuterium arc lamp, a metal-halide arc lamp, a ceramic xenon lamp, a gas-discharge lamp, a high intensity pulse lamp, a UV LED, a UV laser, a synchrotron light source, and the like.

In some instances, a disinfecting device disclosed herein comprises only a single light source. In some instances, a disinfecting device disclosed herein comprises two or more light sources. A disinfecting light source of the present invention may include any shape, configuration or layout compatible for use in achieving the intended operation of a disinfection device disclosed herein. For example, in some instances a light source comprises at least one of a linear, spiral, toroid, or serpentine lamp configuration. A light source may further include a housing window comprising one or more desired optical materials, such as a quarts, suprasil, or sapphire housing window.

In some instances, a container is disinfected when exposed to an antimicrobial wavelength emitted by the light source as the container passes through the interior of the disinfecting device. In some instances, a container is entirely disinfected (i.e. sterilized) after passing through the disinfecting device one time. In some instances, a container is partially disinfected (i.e., sanitized) after passing through the disinfecting device one time, and is entirely disinfected (i.e., sterilized) after passing through the disinfecting device two or more times, wherein each subsequent passage of the container through the disinfecting device cumulatively sanitized and/or disinfects the container. In some instances, a container is progressively sanitized via subsequent passes through the interior of the disinfecting device.

A disinfecting device disclosed herein may include various additional components, circuitry, software, hardware, drivers, sensors, blowers, ventilation, filters, motors, drive belts, and the like as may be required to provide an operable disinfecting device. A disinfecting device herein may further be modified to include various additional components, circuitry, software, hardware, drivers, sensors, blowers, ventilation, filters, motors, drive belts, and the like that may be desired to accommodate and adapt a disinfecting device for use with a new security screening system, an existing security screening system, or a component of a new or existing security screening system.

In some instances, a disinfecting device disclosed herein is provided as part of a security screening system (such as a security screening system at an airport), wherein the device is positioned at a location in the security screening system where a container, comprising a security bin, is free of any personal items (i.e., it is empty). The security bin is passed through the interior of the disinfecting device and disinfected by one or more antimicrobial wavelengths emitted by the disinfecting light source. The security bin then exits the disinfecting device and is collected. In some instances, the security bins exit the disinfecting device at the beginning of the security screening system. In some instances, the collected security bins exit the disinfecting device at the end of the security screening system and are manually shuttled to the beginning of the security screening system for continued use. In some instances, a security screening system comprises an auto-return system of rollers and/or conveyor belts to automatically collect and shuttle the disinfected security bins to the beginning of the security screening system.

In some instances, the present invention further comprises a method for disinfecting a container using a disinfecting device disclosed herein.

BRIEF DESCRIPTION OF THE DRAWINGS

It will be appreciated by those of ordinary skill in the art that the various drawings are for illustrative purposes only. The nature of the present invention, as well as other embodiments of the present invention, may be more clearly understood by reference to the brief and detailed descriptions of the invention, to the appended claims, and to the several drawings.

FIG. 4F is a cross-sectioned side view of a disinfecting device having a first security bin in a cantilevered position, a second security bin at an "active" position, and a third security bin partially at a "dead" position in accordance with a representative embodiment of the present invention.

DETAILED DESCRIPTION OF THE INVENTION

Figure 1A:
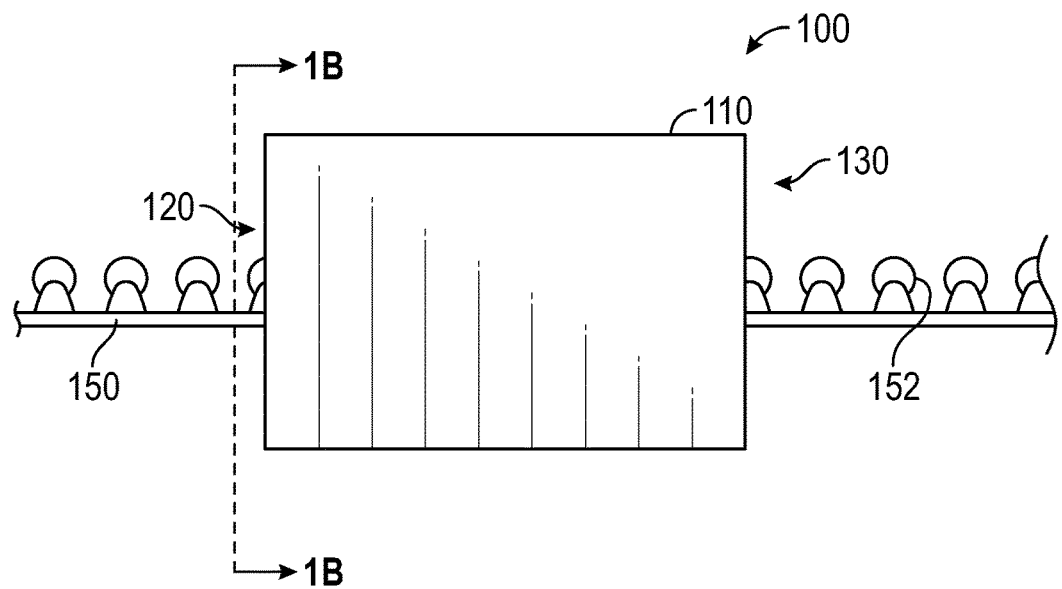
FIG. 1A is side view of a disinfecting device in accordance with a representative embodiment of the present invention.
Figure 1B:
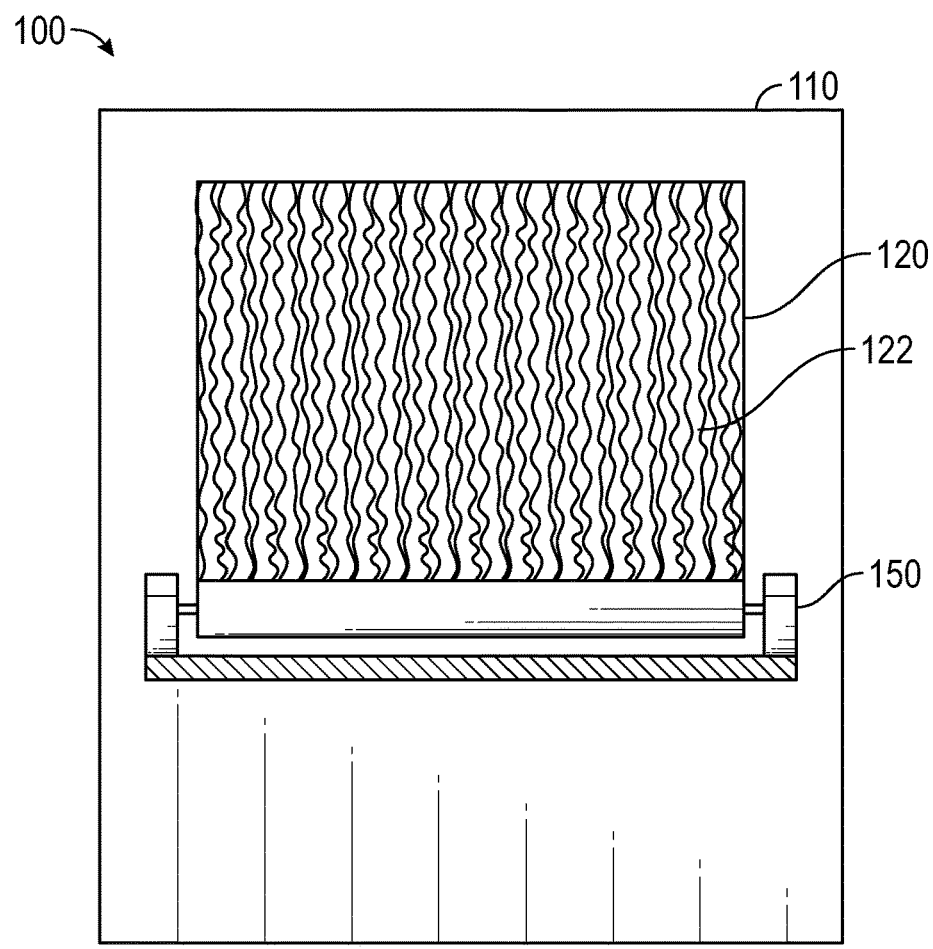
FIG. 1B is a partially cross-sectioned view of a disinfecting device in accordance with a representative embodiment of the present invention.
Figure 1C:
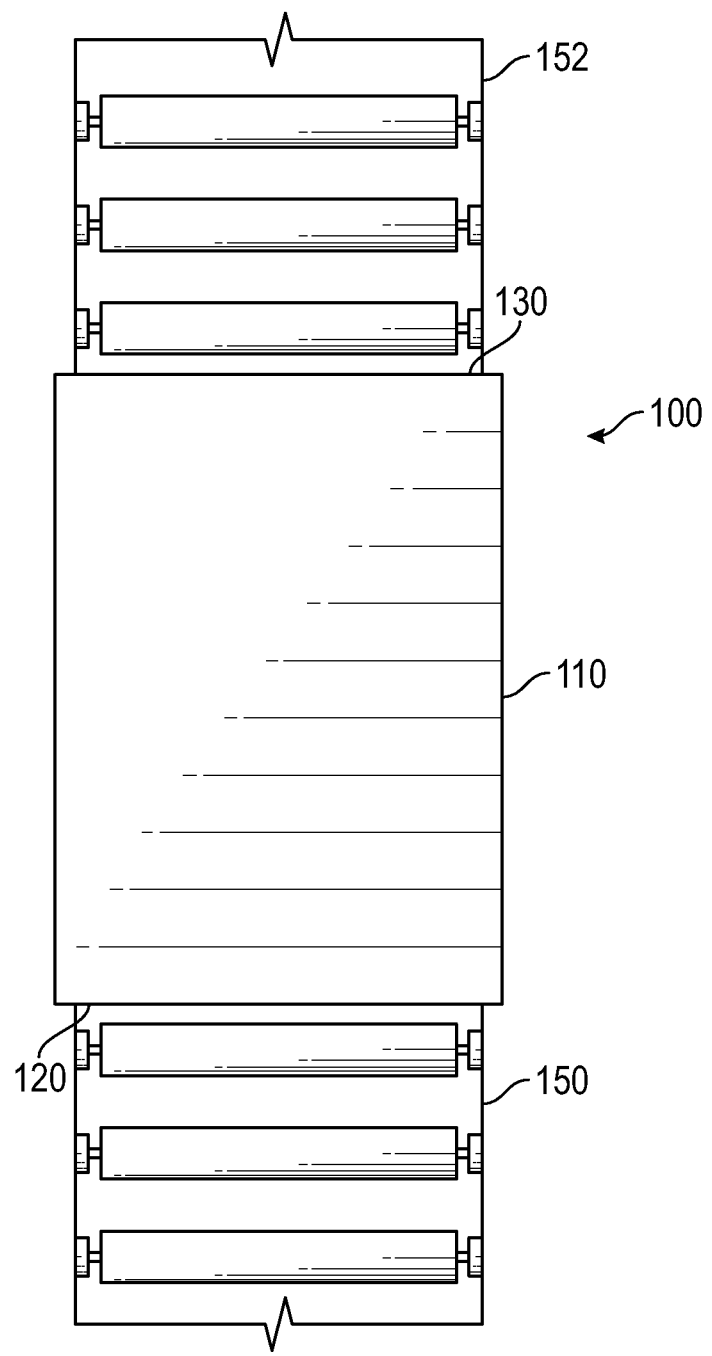
FIG. 1C is a top view of a disinfecting device in accordance with a representative embodiment of the present invention.

Referring now to FIGS. 1A-1C, a disinfecting device 100 is shown. Disinfecting device 100 is configured for use in disinfecting a security bin. Disinfecting device 100 comprises a housing 110 in which various components of disinfecting device 100 are positioned. Housing 110 may comprise any material compatible for use with the present invention. In some embodiments, housing 110 comprises a structurally rigid material that is opaque. Non-limiting examples of compatible materials for housing 110 include metals, colored plastics, and composites. In at least one embodiment of the present invention, housing 110 comprises a sheet metal material, such as steel, stainless steel, or aluminum. In some embodiments, housing 110 may comprise an exterior material having a first property or function, and an interior material having a second property or function that is different than the first property or function. For example, in at least one embodiment of the present invention, housing 110 comprises a exterior material that is structurally rigid and opaque, and further comprises an interior material that is reflective. In some embodiments, an interior material of housing 110 is a coating applied to an inner surface of an exterior material of housing 110.

Housing 110 of disinfecting device 100 may comprise any shape, size and/or configuration compatible for use with the present invention. In some embodiments, housing 110 comprises a cube or cuboid shape. In some embodiments, housing comprises at least one nonlinear surface, shape, or profile. In some embodiments, housing 110 comprises an exterior shape that mirrors an interior shape of housing 110. In some embodiments, housing 110 comprises an exterior shape that is different than an interior shape of housing 110. Housing 110 may further comprise a variety of surfaces or other structural features configured to receive various components of disinfecting device 100. For example, housing 110 may comprise any combinations of clips, slots, receptacles, threaded connections, threaded openings, screws, bolts, nuts, mounts, adhesives, channels, grooves, circuitry, bosses, and the like. Disinfecting device 100 may comprise various features, structures, and other elements as may be desired, or required, to accommodate a variety of security bin sizes, structural features, surfaces, configurations, and the like.

Housing 110 further comprises an upstream opening 120, a downstream opening or exit 130, and a pathway extending therebetween. Openings 120 and 130 may comprise any shape and dimensions compatible for permitting passage of a security bin therethrough. In some embodiments, openings 120 and 130 are rectangular. In some embodiments, the dimensions of openings 120 and/or 130 are selected to minimize a distance or gap between the opening and at least one surface of a security bin when passed through the opening.

Upstream and downstream openings 120 and 130 further comprise a covering 122. Covering 122 is generally provided as a light shield configured to retain or substantially retain antimicrobial wavelengths within the interior of housing 110. In some embodiments, covering 122 is a brush seal having a plurality of bristles that may be temporarily displaced by a security bin being advanced through openings 120 and/or 130. In some embodiments, covering 122 comprises a plastic strip door or curtain having a plurality of opaque or light-filtering strips that may be temporarily displaced by a security bin being advanced through opening 120 and/or 130. In at least one embodiment, covering 122 comprises a plastic strip door comprising a polymer that filters, absorbs and/or scatters electromagnetic wavelengths less than approximately 400 nm and greater than approximately 1000 nm. In some embodiments, covering 122 comprises a polarized polymer material. In some embodiments, covering 122 comprises one or more light blocking polymer additives. In some embodiments, a covering 122 for each opening 120 and 130 comprises two or more barriers or layers positioned in and/or in proximity to a respective opening. In some embodiments, a space, gap or distance is provided between two adjacent barriers or layers of a covering 122. In some embodiments, covering 122 comprises a solid door or curtain that is automatically driven between closed and open positions by a mechanical means, which may include at least one of a motor, a hinge, a driver, a sensor, a bearing, a chassis, a pivot, a driveshaft, suspension, an actuator, and/or the like.

In some embodiments, disinfecting device 100 is a stand-alone unit having various features and designs intended for use independent of any other equipment. In some embodiments, disinfecting device 100 is an integrated, inline component of a security screening system. In some embodiments, disinfecting device 100 is a modular component that may be added or removed, as desired, from a security screening system.

Disinfecting device 100 may further be used in combination with a conveyor. In some embodiments, a conveyor is provided to convey a security bin through an interior of device 100. In some embodiments, a conveyor is used to deliver a security bin to device 100. In some embodiments, a conveyor is used to retrieve a security bin from device 100.

Non-limiting examples of compatible conveyors include belt conveyors, gravity roller conveyors, chain conveyors, live roller conveyors, chain driven live roller conveyors, belt driven live roller conveyors, motorized roller conveyors, slat conveyors, beam trolley systems, overhead conveyors, power conveyors, free conveyors, hand push conveyors, over under conveyors, and inverted conveyors. In some embodiments, disinfecting device 100 is used with two or more conveyors.

In some embodiments, disinfecting device 100 is used in combination with an inbound conveyor 150 configured to deliver a security bin to upstream opening 120. In some embodiments, disinfecting device 100 is used in combination with an internal conveyor configured to move a security bin through the pathway of housing 110. In some embodiments, disinfecting device 100 is used in combination with an outbound conveyor configured to receive and move a security bin which has exited the downstream opening 130 of disinfecting device 100.

In some embodiments, disinfecting device 100 comprises a single conveyor configured to perform inbound, outbound and interior transportation of a security bin through disinfecting device 100. In some embodiments, a disinfecting device of the present invention is used in combination with a conveyor component of a security screening system. In some embodiments, a disinfecting device of the present invention is used in combination with an outbound conveyor configured to automatically transport a security bin to a starting point in security screening system, wherein disinfecting device 100 is integrated or otherwise incorporated into an automated security bin management system. In some embodiments, disinfecting device 100 may be integrated into any desired system or configuration.

Referring now to FIGS. 2A-2E a disinfecting device 200 is shown, wherein a side panel of housing 210 has been removed to provide a view of the housing interior 212. In some embodiments, a disinfecting device 200 is provided having one or more features or elements of disinfecting device 100, described above. In some embodiments, disinfecting device 200 is a cross-sectioned representation of disinfecting device 100, wherein equivalent features or elements of disinfecting device 100 are shown with disinfecting device 200.

In some embodiments, housing 210 comprises an interior 212 in which is housed various components for use in transporting and disinfecting a security bin 290 that travels therethrough. In some embodiments, interior 212 comprises an interior conveyor 254 that actively moves security bin 290 through interior 212. Interior conveyor 254 comprises an upstream end 256 positioned in proximity to upstream opening 220 and configured to receive a security bin 290 from an upstream source, such as, for example, an inbound conveyor 250. In some embodiments, upstream end 256 is approximately level or even with inbound conveyor 250. Interior conveyor 254 further comprises a downstream end 258 positioned in proximity to downstream opening 230 and configured to transfer a security bin 290 from interior conveyor 254 to a downstream source, such as, for example, an outbound conveyor 252. In some embodiments, downstream end 258 is approximately level or even with outbound conveyor 252.

In some embodiments, interior conveyor 254 is a motor-driven conveyor, either directly motor driven, or indirectly motor driven, such as by a motor-driven belt or chain. In some embodiments, interior conveyor 254 is driven by upstream and/or downstream conveyor 250, 252, or a motor that is used to drive upstream and/or downstream conveyors 250, 252. In some embodiments, interior conveyor 254 is configured to transport security bin 290 through the interior 212 of housing 210 at a desired speed. In some embodiments, a speed of interior conveyor 254 is selected to achieve a desired duration of travel for security bin 290 through housing 210. In some embodiments, a speed of interior conveyor 254 is selected to achieve a duration of travel for security bin 290 through housing 210 of approximately less than 1 second, of approximately 1 second, of approximately 1 to 3 second, of approximately 1 to 5 seconds, of approximately 1 to 10 seconds, of approximately 1 to 30 seconds, or greater than 30 seconds.

In some embodiments, interior conveyor 254 is at least partially transparent to permit the passage of light therethrough while simultaneously transporting a security bin 290 through interior 212 of housing 210. In some embodiments, interior conveyor 254 comprises a plurality of rails 260 that are spaced apart such that gaps 262 are provided between adjacent rails, wherein at least some exterior surfaces of security bin 290 are exposed to light that passes through these gaps 262. In some embodiments, rails 260 comprise a material that is optically translucent or optically clear, for example a polymer material or a glass material. For these embodiments, the optically translucent or optically clear properties of rails 260 permits light to travel through rails 260. In some embodiments, interior conveyor 254 comprises a wire belt, wherein rails 260 comprise wire rods or a wire mesh collectively having a minimal surface area as compared to the collective surface area of gaps 262. In some embodiments, interior conveyor 254 comprises a belt conveyor, wherein the belt comprises an optically translucent or optically clear material.

Disinfecting device 200 further comprises at least one light source 270 configured to disinfect at least one surface of security bin 290 as it passes through interior 212 of housing 210. In some embodiments, disinfecting device 200 comprises two light sources 270. In some embodiments, disinfecting device 200 comprises more than two light sources 270. In some embodiments, light source 270 is a disinfecting light source. In some embodiments, light source 270 is a sanitizing light source.

Light source 270 may comprise any compatible device or combination of compatible devices capable of emitting an antimicrobial wavelength. As used herein, the term "antimicrobial wavelength" is understood to include any electromagnetic wavelength that is lethal to a microbe, including, but not limited to a biological function of a specific electromagnetic wavelength, or range of electromagnetic wavelengths, as well as an intensity and/or a duration of emittance of the antimicrobial wavelength to a microbe. In some embodiments, light source 270 is configured to emit a single antimicrobial wavelength. In some embodiments, light source 270 is configured to emit two or more antimicrobial wavelengths. In some embodiments, light source 270 is configured to emit a range of antimicrobial wavelengths. In some embodiments, light source 270 emits two or more antimicrobial wavelengths concomitantly. In some embodiments, light source 270 emits two or more antimicrobial wavelengths in an ordered succession. In some embodiments, light source 270 emits two or more antimicrobial wavelengths in a random succession.

In some embodiments, light source 270 emits an antimicrobial wavelength of from approximately less than 1 nm to less than 1000 nm, of from approximately 1-1000 nm, of from approximately 10-900 nm, of from approximately 100-800 nm, of from approximately 200-800 nm, of from approximately 300-800 nm, or from approximately 390-750 nm.

In some embodiments, light source 270 emits an antimicrobial wavelength at a high intensity of from 1-2000 joules, of from 10-1900 joules, of from 50-1850 joules, of from 75-1800 joules, of from 100-1750 joules, of from 150-1700 joules, of from 200-1650 joules, of from 300-1600 joules, of from 400-1500 joules, of from 500-1400 joules, of from 600-1300 joules, of from 700-1200 joules, or from 800-1000 joules.

In some embodiments, light source 270 emits an antimicrobial wavelength at a pulse duration of from 1-1000 msec, of from 10-950 msec, of from 20-900 msec, of from 25-850 msec, of from 30-800 msec, of from 50-750 msec, of from 75-700 msec, of from 100-650 msec, of from 150-600 msec, of from 200-550 msec, of from 300-500 msec, or from 350-450 msec.

In some embodiments, light source 270 emits an antimicrobial wavelength at a pulse duration of from 1-1000 msec, of from 10-950 msec, of from 20-900 msec, of from 25-850 msec, of from 30-800 msec, of from 50-750 msec, of from 75-700 msec, of from 100-650 msec, of from 150-600 msec, of from 200-550 msec, of from 300-500 msec, or from 350-450 msec, and at an intensity of from 1-2000 joules/pulse, of from 10-1900 joules/pulse, of from 50-1850 joules/pulse, of from 75-1800 joules/pulse, of from 100-1750 joules/pulse, of from 150-1700 joules/pulse, of from 200-1650 joules/pulse, of from 300-1600 joules/pulse, of from 400-1500 joules/pulse, of from 500-1400 joules/pulse, of from 600-1300 joules/pulse, of from 700-1200 joules/pulse, or from 800-1000 joules/pulse. In some embodiments, light source 270 emits an antimicrobial wavelength at an intensity of approximately 505 joules/pulse.

In some embodiments, light source 270 emits a pulsed antimicrobial wavelength, wherein the time between two pulses (or voltage signals) is approximately 0.05 seconds, 0.1 seconds, 0.15 seconds, 0.18 seconds, 0.2 seconds, 0.25 seconds, 0.3 seconds, 0.35 seconds, 0.4 seconds, 0.45 seconds, or 0.5 seconds. In some instances, a light source is provided configured to emit a pulsed antimicrobial wavelength at 1 pulse per second, 2 pulses per second, 3 pulses per second, 4 pulses per second, 5 pulses per second, 6 pulses per second, 7 pulses per second, 8 pulses per second, 9 pulses per second, 10 pulses per second, 11 pulses per second, 12 pulses per second, 13 pulses per second, 14 pulses per second, 15 pulses per second, or greater than 15 pulses per second.

In some embodiments, light source 270 is configured to emit a desired number of pulses of an antimicrobial wavelength onto a surface of security bin 290 while being conveyed or otherwise passed through interior 212. In some embodiments, the desired number of pulses is selected to disinfect the surface of the security bin 290. In some embodiments, the desired number of pulses is selected to sanitize the surface of the security bin 290. In some embodiments, a desired number of pulses is 1 pulse, 2 pulses, 3 pulses, 4 pulses, 5 pulses, 6 pulses, 7 pulses, 8 pulses, 9 pulses, 10 pulses, 1 to 10 pulses, 1 to 20 pulses, 1 to 30 pulses, 1 to 50 pulses, 1 to 60 pulses, approximately 10 pulses, approximately 20 pulses, approximately 30 pulses, approximately 40 pulses, approximately 50 pulses, approximately 60 pulses, approximately 100 pulses, approximately 300 pulses, approximately 500 pulses, approximately 750 pulses, approximately 1000 pulses, or greater than 1000 pulses.

In some embodiments, light source 270 emits an antimicrobial wavelength effective in eliminating at least one microbe selected from the group consisting of *Staphylococcus aureus* (MRSA), *Pseudomonas aeruginosa*, *Streptococcus pyogenes*, *Mycobacterium tuberculosis*, *Klebsiella pneumoniae*, *Escherichia coli*, *Clostridium difficile*, *Neisseria gonorrhoeae*, *Aceinetobacter baumannii*, and *Burkholderia cepacia*. In some embodiments, light source 270 emits an antimicrobial wavelength effective in eliminating a virus. In some embodiments, light source 270 emits an antimicrobial wavelength effective in eliminating a bacteria. In some embodiments, light source 270 emits an antimicrobial wavelength effective in eliminating a parasite. In some embodiments, light source 270 emits an antimicrobial wavelength effective in eliminating one or more of the foregoing microbes from a surface of security bin 290.

In some embodiments, light source 270 is configured to emit an antimicrobial wavelength over a period of time sufficient to sanitize and/or disinfect at least one surface, or a portion of at least one surface of a security bin 290 as it passes through interior 212 of housing 210. In some embodiments, light source 270 emits an antimicrobial wavelength over a period of time of less than 1 second, approximately 1 second, approximately 2 seconds, approximately 3 seconds, approximately 4 seconds, approximately 5 seconds, approximately 6 seconds, approximately 7 seconds, approximately 8 seconds, approximately 9 seconds, approximately 10 seconds, or greater than 10 seconds. In some embodiments, light source 270 emits an antimicrobial wavelength over a period of time greater than 0 seconds and less than or equal to 1 second.

In some embodiments, light source 270 is a pulsed gas discharge lamp. In some embodiments, light source 270 is a xenon flash lamp. In some embodiments, light source 270 is a cathode ray tube. In some embodiments, light source 270 is a laser. In some embodiments, light source 270 is a high-intensity discharge lamp. In some embodiments, light source 270 is a high pressure gas discharge lamp. In some embodiments, light source 270 is a low pressure discharge lamp. In some embodiments, light source 270 is a LED. In some embodiments, light source 270 emits UV radiation.

In some embodiments, a surface of security bin 290 is entirely disinfected through a single exposure to an antimicrobial wavelength emitted from a light source 270 of the present invention. In some embodiments, a surface of a security bin 290 is substantially disinfected through a single exposure to an antimicrobial wavelength emitted from a light source 270 of the present invention. In some embodiments, a surface of security bin 290 is entirely disinfected through two or more exposures to an antimicrobial wavelength emitted from a light source 270 of the present invention. In some embodiments, a surface of security bin 290 is cumulatively disinfected through two or more subsequent exposures to an antimicrobial wavelength emitted from a light source 270 of the present invention. In some embodiments, a surface of security bin 290 is sanitized through one or more exposures to an antimicrobial wavelength emitted from a light source 270 of the present invention. In some embodiments, a surface of security bin 290 is sanitized or disinfected by passing through disinfecting device 200 one time. In some embodiments, a surface of security bin 290 is sanitized or disinfected by passing through disinfecting device 200 more than one time.

Light source 270 may comprise any size, shape, configuration and/or layout compatible with the present invention. In some embodiments, light source 270 comprises at least one of a linear, round, tubular, spiral, toroid, or serpentine lamp configuration. In some embodiments, light source 270 comprise a linear tube. In some embodiments, light source 270 comprises a toroid having a central opening through which interior conveyor 254 passes, such that light source 270 provides approximately 360° of exposure of an antimicrobial wavelength to security bin 290. In some embodiments, at least one of a size, shape, configuration and/or layout of light source 270 is selected to optimize exposure of security bin 290 to an antimicrobial wavelength emitted from light source 270.

In some embodiments, light source 270 includes a housing window comprising one or more desired optical materials, such as a quarts, suprasil, or sapphire housing window. In some embodiments, a housing window of light source 270 is selected to filter (i.e., absorb or scatter) at least one undesired wavelength. In some embodiments, a housing window of light source 270 is selected to focus at least one antimicrobial wavelength emitted from light source 270.

In some embodiments, light source 270 is located within interior 212 at a position that is below interior conveyor 254, such that an exterior surface of security bin 290 is exposed to an antimicrobial wavelength emitted from light source 270 as the security bin 290 passes over light source 270. In some embodiments, light source 270 is located within interior 212 at a position that is above interior conveyor 254, such than an interior surface of security bin 290 is exposed to an antimicrobial wavelength emitted from light source 270 as the security bin 290 passes under light source 270. In some embodiments, first and second light sources 270 are position below and above interior conveyor 254 to simultaneously emit an antimicrobial wavelength on exterior and interior surfaces of security bin 290. In some embodiments, a plurality of light sources 270 are provided to ensure exposure of an antimicrobial wavelength to all or substantially all surfaces of security bin 290. For example, in some embodiments light source 270 comprises one, two, three, four, or more than four light sources. In some embodiments, light source 270 comprises a plurality of identical types of light sources. In some embodiments, light source 270 comprises a plurality of different types of light sources.

In some embodiments, a surface of interior 212 further comprises a reflective coating or material 280 positioned opposite light source 270, wherein reflective coating 280 reflects the emitted antimicrobial wavelength onto at least one surface of security bin 290 that is not directly exposed to light source 270. In some embodiments, disinfecting device 200 further comprises a reflector 282 strategically positioned within interior 212 so as to deflect or otherwise direct an antimicrobial wavelength emitted from light source 270 onto at least one surface of security bin 290 that may or may not be directly exposed to light source 270. For example, in some embodiments light source 270 is located at a position below security bin 290, and one or more reflectors 280 and/or 282 is positioned to deflect an antimicrobial wavelength emitted from light source 270 onto the side and/or interior surfaces of security bin 290. In some embodiments, reflector 280 and/or 282 is a mirror. In some embodiments, a reflector is a fiber optic filament or bundle of fiber optic filaments.

In some embodiments, disinfecting device 200 further comprises various supporting components, circuitry, software, hardware, computer devices, drivers, blowers, ventilation, filters, and the like as may be required, or desired, for use with light source 270. In some embodiments, light source 270 is provided as part of a lighting system that includes a variety of components specifically designed for use with light source 270. In some embodiments, disinfecting device 200 is compatible for use with an existing lighting system comprising a desired light source 270. In some embodiments, light source 270 is plug-and-play compatible with disinfecting device 200. In some embodiments, disinfecting device 200 is compatible for use with a single type or make of light source 270. In some embodiments, disinfecting device 200 is compatible for use with a variety of different types or makes of light source 270.

In some embodiments, housing 210 further comprises one or more sensors 284 strategically positioned within interior 212 and configured to determine a position of security bin 290 within interior 212. In some embodiments, sensors 284 are further provided to determine a timing of exposure and/or a duration of exposure of security bin 290 to an antimicrobial wavelength emitted from light source 270. Sensor 284 may comprise any sensor technology compatible with the present invention. In some embodiments, sensor 284 is a laser sensor. In some embodiments, sensor 284 is an infrared sensor. In some embodiments, sensor 284 is a light curtain. In some embodiments, sensor 284 is a physical switch positioned in the path of security bin 290 such that sensor 284 is directly or indirectly contacted by security bin 290 when located within interior 212. In some embodiments, sensor 284 directly senses security bin 290. In some embodiments, sensor 284 detects a light level within interior 212, such that when upstream and downstream coverings 224, 226 are temporarily defeated by security bin 290, ambient light leaked therethrough is detected. In some embodiments, sensor 284 is used to determine a duration of exposure and/or a timing of exposure of security bin 290 to an antimicrobial wavelength emitted from light source 270.

In some embodiments, sensor 284 comprises a plurality of sensors positioned within interior 212 at strategic positions to determine an optimal position of security bin 290 relative to light source 270. In some embodiments, an upstream sensor 284a is placed in proximity to upstream opening 220 such that upstream sensor 284a senses when security bin 290 has entered interior 212 via upstream opening 220. In some embodiments, a downstream sensor 284b is placed in proximity to downstream opening 230 such that downstream sensor 284b senses when security bin 290 is near downstream opening 230. Sensors 284 may further be configured to detect other various metrics and/or parameters of disinfecting device 200, such as temperature, air quality, the presence of trace explosives, total number of security bins passed through disinfecting device 200, total number of light pulses from light source 270, a speed at which security bin 290 passes through disinfecting device 200, and the like.

Figure 2A:
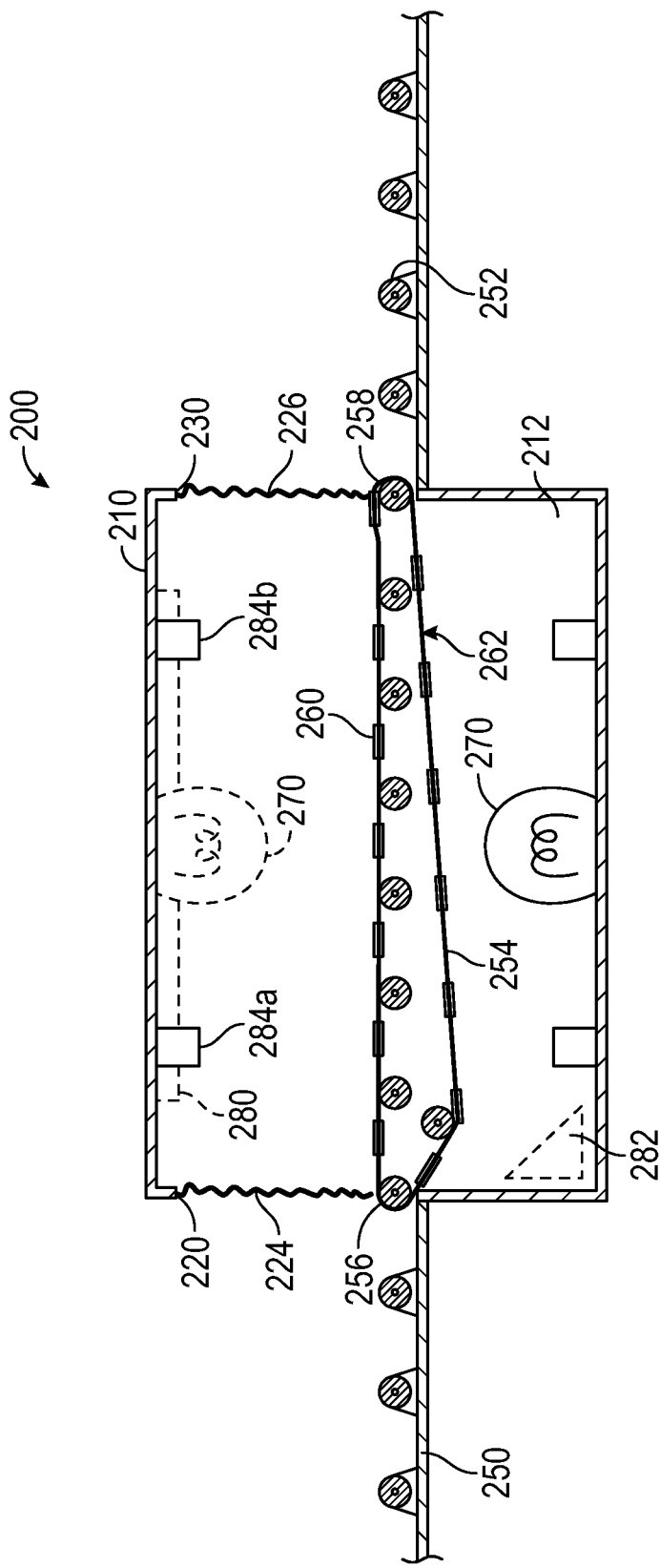
FIG. 2A is a cross-sectioned side view of a disinfecting device in accordance with a representative embodiment of the present invention.

Referring now to FIG. 2A, a cross-section side view of disinfecting device 200 is shown in an inactive, resting, or ready state, wherein interior 212 does not contain a security bin 290. In this embodiment, disinfecting device 200 is used in combination with an inbound conveyor 250 coupled to or placed in proximity to upstream opening 220, and further in combination with an outbound conveyor 252 coupled to or placed in proximity to downstream opening 230. In some embodiments, light source(s) 270 does not emit light when disinfecting device 200 is in the inactive, resting, or ready state, however various other components of device 200 may be active, for example pathway conveyor 254 may run while in the ready state. Other components such as sensors 284, cooling fans, vents, circuitry, and other electrical components may run while in the ready state.

Figure 2B:
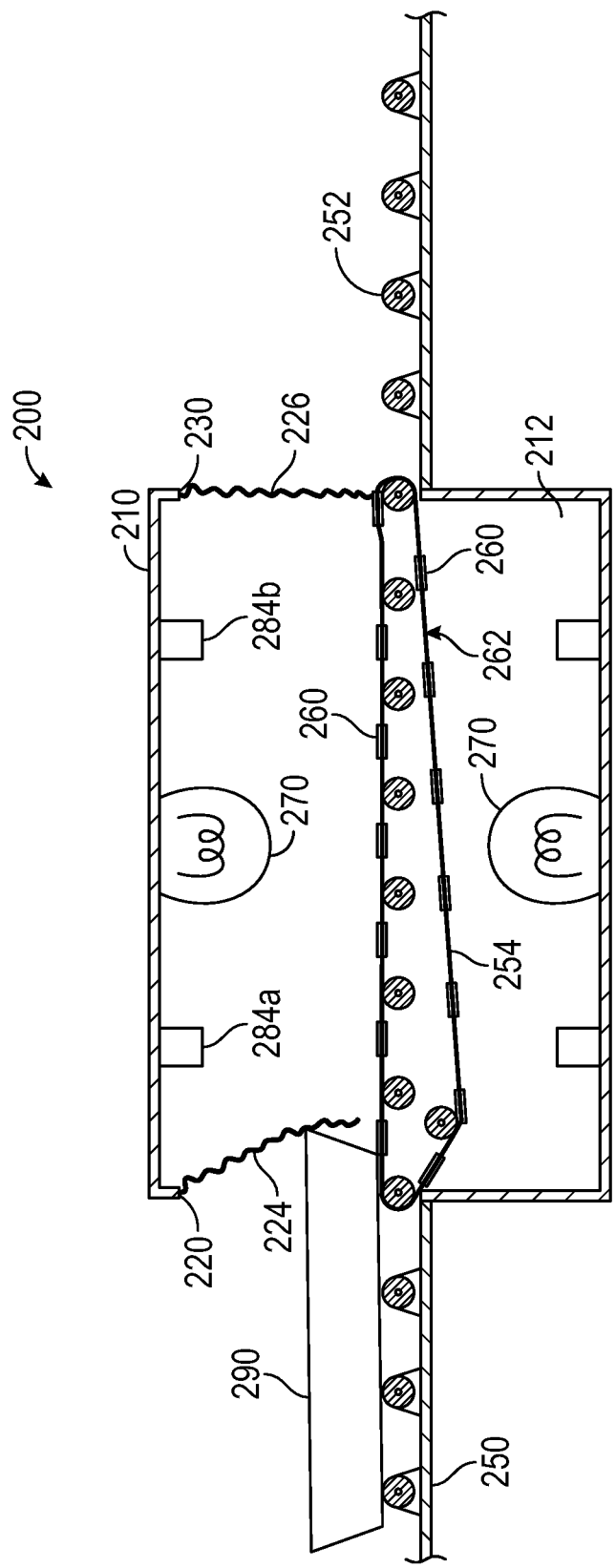
FIG. 2B is a cross-sectioned side view of a disinfecting device illustrating a security bin partially inserted through an opening of the disinfecting device in accordance with a representative embodiment of the present invention.

Referring now to FIG. 2B, a cross-section side view of disinfecting device 200 is shown in a pre-active state, wherein upstream covering 224 has been breached by security bin 290 but security bin 290 is not fully located within interior 212. In some embodiments, light source(s) 270 does not emit light when disinfecting device 200 is in the pre-active state, however various other components of device 200 may be active, as described above. In some embodiments, one or more sensors 284 detect the pre-active state, such as by sensing the motion of security bin 290 and/or upstream covering 224, or detecting light leaked through upstream opening 220. In some embodiments, detection of pre-active state by sensor 284 is used to set a timing for turning on light source 270.

Figure 2C:
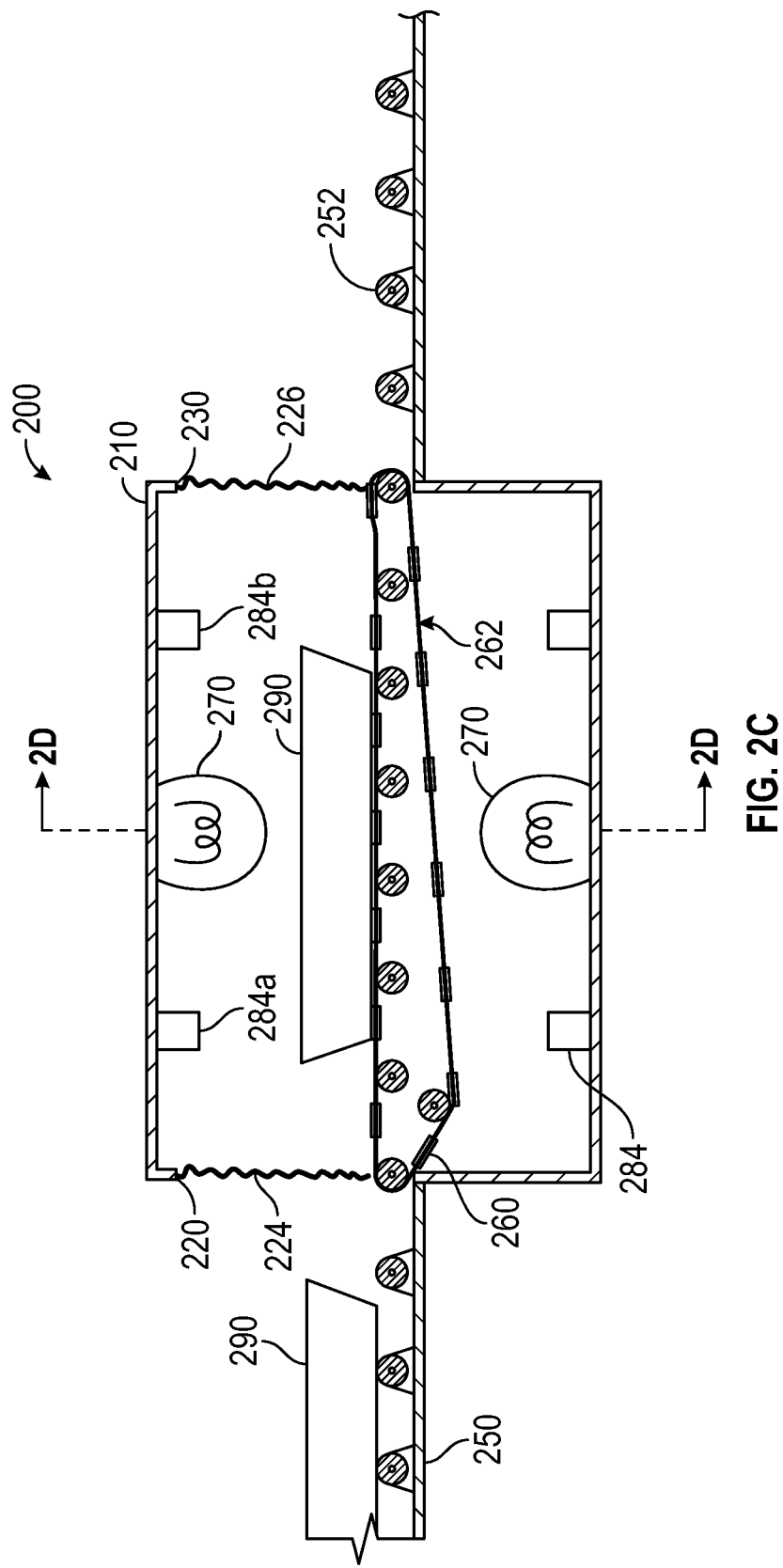
FIG. 2C is a cross-sectioned side view of a disinfecting device illustrating a security bin fully inserted within the disinfecting device in accordance with a representative embodiment of the present invention.

Referring now to FIG. 2C, a cross-section side view of disinfecting device 200 is shown in an active state, wherein security bin 290 is entirely positioned within interior 212. In some embodiments, the active state is further characterized by upstream and downstream coverings 224, 226 being in a closed position. In some embodiments, the active state is initiated when security bin 290 is sensed simultaneously by upstream and downstream sensors 284a and 284b. In some embodiments, the active state is initiated when a sensor 284 senses a light level of interior 212 which suggests upstream and downstream coverings 224, 226 are in a closed position. In some embodiments, the active state is initiated when security bin 290 is not sensed by upstream sensor 284a, but is sensed by downstream sensor 284b.

In the active state, light source(s) 270 are activated, whereby security bin 290 is exposed to an antimicrobial wavelength emitted therefrom. In some embodiments, the duration of the active state is the time required to move security bin 290 through interior 212. In some embodiments, the duration of the active state is extended by temporarily pausing pathway conveyor 254, such that the duration of exposure of security bin 290 to the antimicrobial wavelengths of light source 270 is extended. In some embodiments, the duration of active state is less than one second, approximately 1 second, approximately 2 seconds, approximately 3 seconds, approximately 4 seconds, approximately 5 seconds, approximately 10 seconds, approximately 15 seconds, approximately 20 seconds, approximately 25 seconds, approximately 30 seconds, or greater than 30 seconds.

Figure 2D:
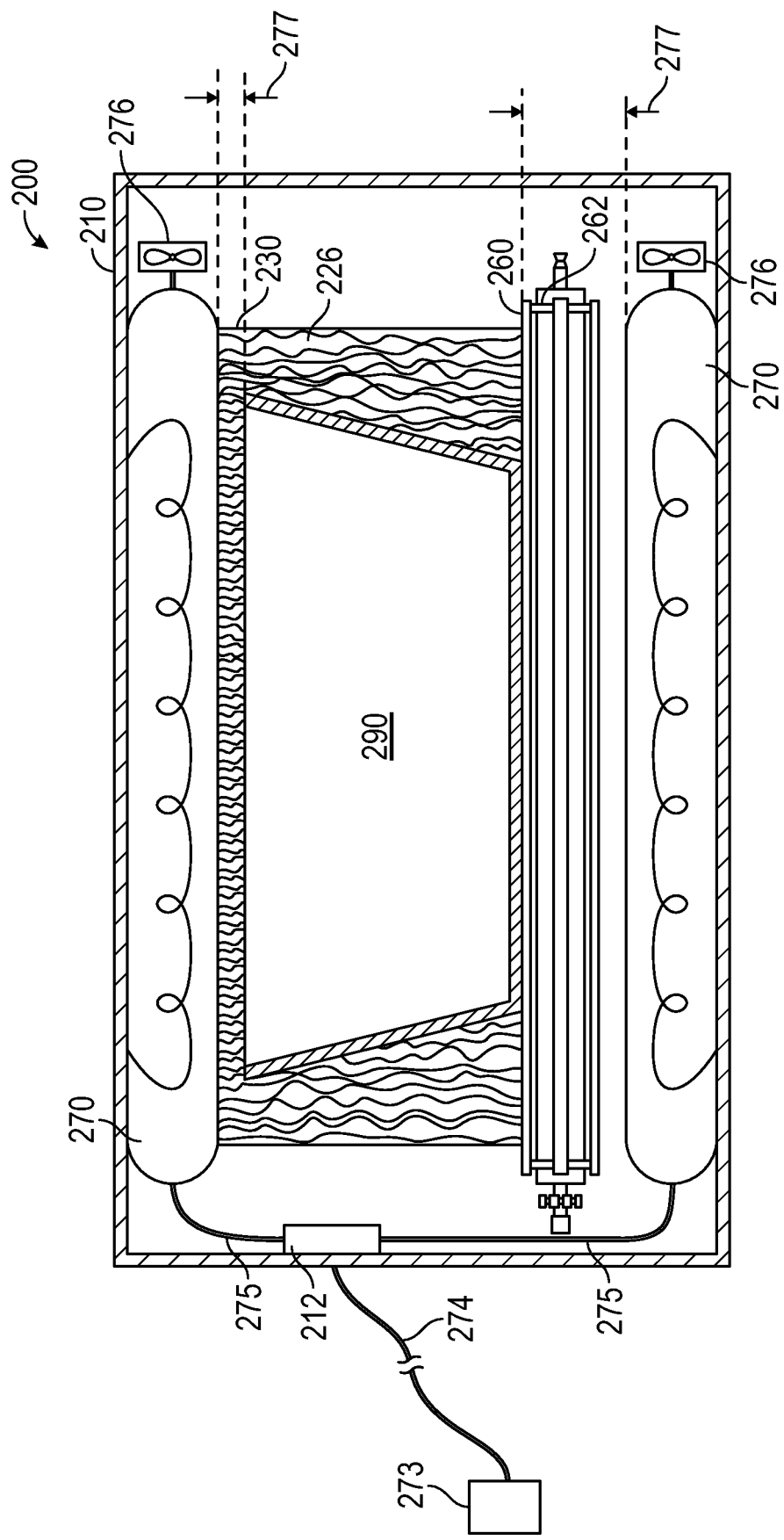
FIG. 2D is a cross-sectioned end view of a disinfecting device illustrating a security bin fully inserted within the disinfecting device in accordance with a representative embodiment of the present invention.

Referring now to FIG. 2D, a cross-section end view of disinfecting device 200 is shown in the active state. In some embodiments, light source(s) 270 further comprises a driver 272 operably connected 274 to a processor 273, such as a computer device. Driver 272 may further be coupled to light sources 270 via circuitry 275. In some embodiments, driver 272 is further operable coupled to a ventilation system of device 200, such as cooling fans 276. In some embodiments, driver 272 and processor 273 are onboard components of disinfecting device 200. In some embodiments, at least one of driver 272 and processor 273 are external components of disinfecting device 200.

In some embodiments, light source 270 is positioned and spaced from a surface of security 290 at a desired distance 277 to optimize exposure coverage and/or the effectiveness of the antimicrobial wavelength emitted from light source 270. In some embodiments, a desired distance 277 is approximately 1 inch, approximately 2 inches, approximately 3 inches, approximately 4 inches, approximately 5 inches, or greater than 5 inches. In some embodiments, distance 277 is 3 inches. In some embodiments, distance 277 is 3 inches or less than 3 inches.

Figure 2E:
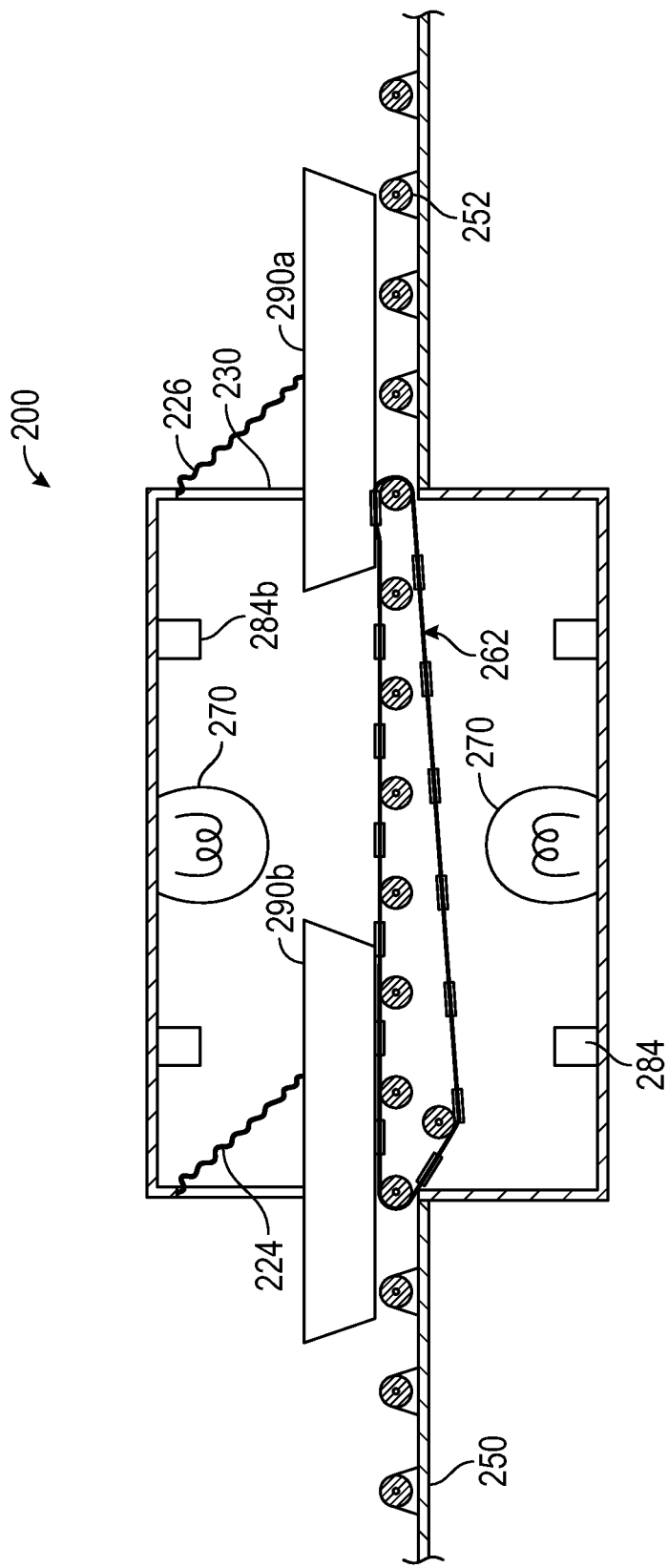
FIG. 2E is a cross-sectioned side view of a disinfecting device illustrating a process by which a plurality of security bins passes through the disinfecting device in accordance with a representative embodiment of the present invention.

Referring now to FIG. 2E, a cross-section side view of disinfecting device 200 is shown in a post-active state, wherein security bin 290*a* has finished being exposed to antimicrobial wavelengths emitted from light source(s) 270 during the active state. In some embodiments, post-active state is further characterized by security bin 290*a* exiting through downstream opening 230. In some embodiments, the post-active state is initiated when security bin 290 is sensed only by downstream sensor 284*a*. In some embodiments, the post-active state is initiated when a sensor 284 senses a light level of interior 212 which suggest at least one of upstream or downstream coverings 224,226 are in an open position. In some embodiments, the post-active state is initiated when security bin 290 is no longer sensed by upstream sensor 284*a*, and continues until security bin 290 is no longer sensed by downstream sensor 284*b*.

In some embodiments, light source(s) 270 does not emit light when disinfecting device 200 is in the post-active state, however various other components of device 200 may be active, as described above. In some embodiments, post-active state of disinfecting device 200 is initiated following an exposure of security bin 290 to an antimicrobial wavelength emitted from light source(s) 270. In some embodiments, post-active state of device 200 is further characterized by upstream covering 224 being breached by an incoming security bin 290*b*. In some embodiments, disinfecting device 200 moves to a ready state at the end of the post-active state, such as when security bin 290*a* exits downstream opening 230 prior to an incoming security bin 290*b* breaching upstream covering 224. In some embodiments, disinfecting device 200 moves to a pre-active state at the end of, or prior to the end of the post-active state, such as when a security bin 290*b* breaches upstream covering 224 while security bin 290*a* is exiting device 200 via downstream opening 230.

Upon exit of security bin 290*a* from downstream opening 230, security bin 290*a* is made available for continued use. In some embodiments, security bin 290*a* is collected at outbound conveyor 252 and subsequently moved to an upstream location for subsequent use. In some embodiments, outbound conveyor 252 is an upstream or starting location of a security screening system. In some embodiments, outbound conveyor 252 is operably connected to a starting location of a security screening system, such that security bins 290*a* are automatically returned to the starting location. In some embodiments, security bins 290*a* are manually collected and transported to the starting location.

Figure 3A:
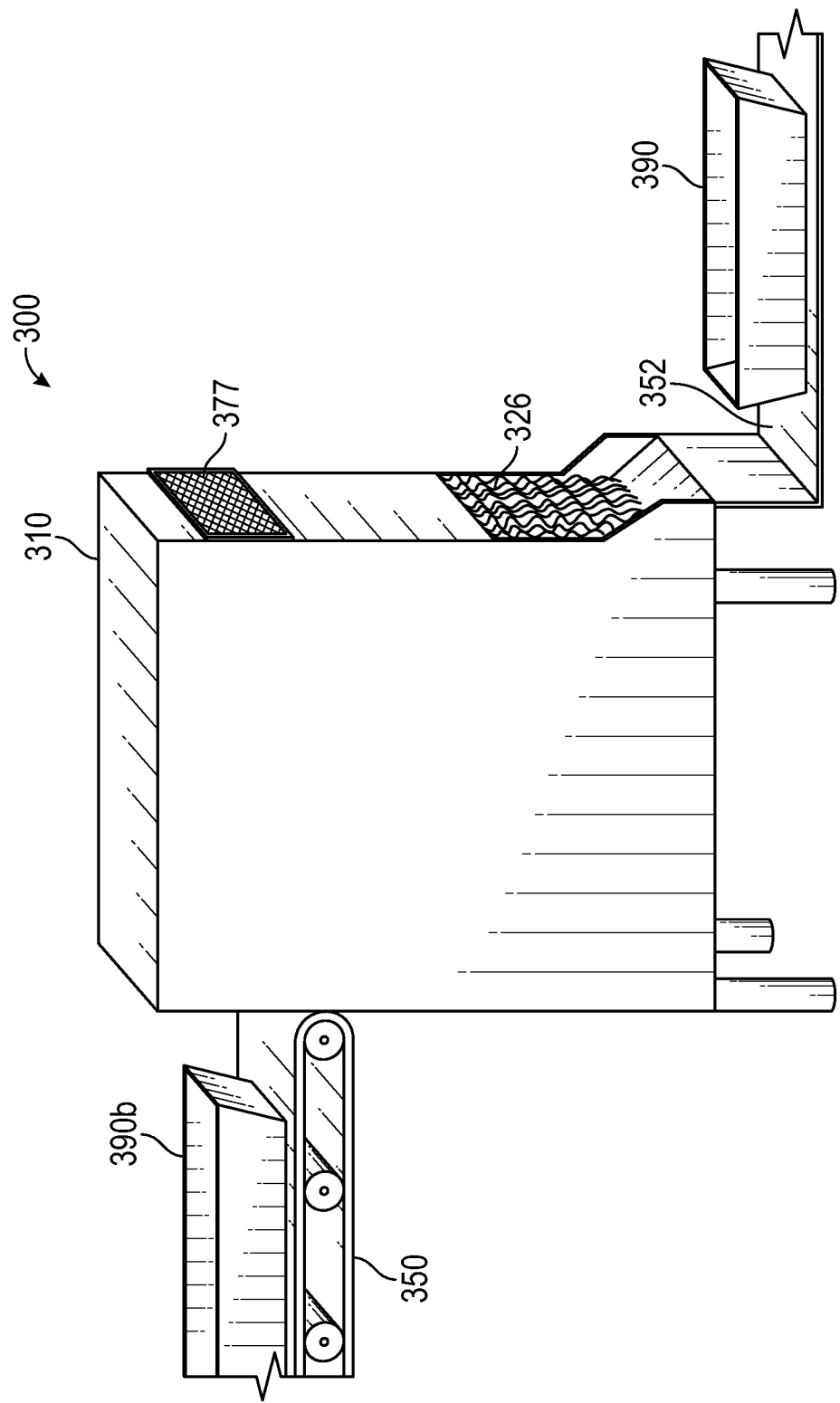
FIG. 3A is a perspective side view of a disinfecting device in accordance with a representative embodiment of the present invention.
Figure 3B:
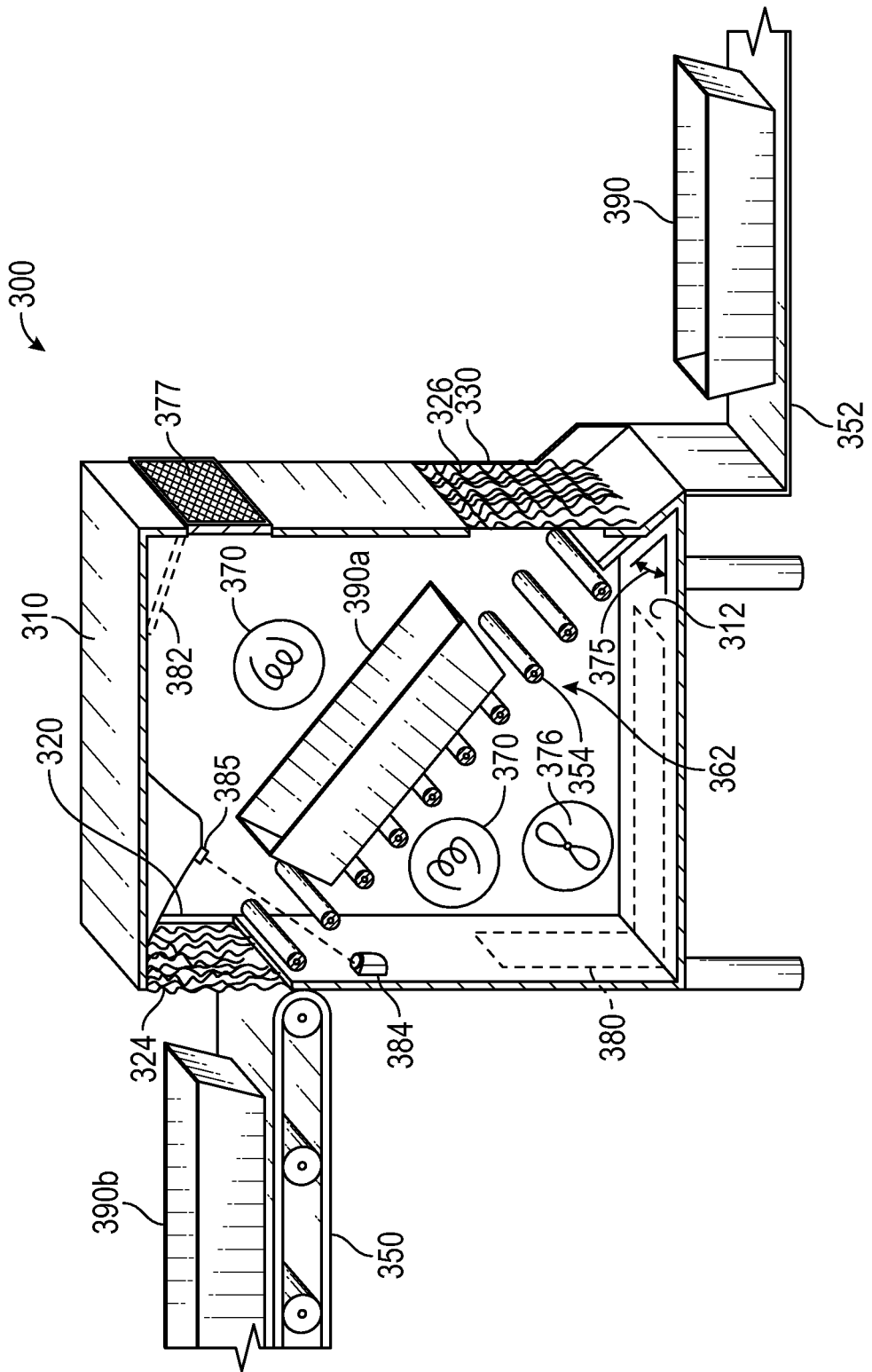
FIG. 3B is a cross-sectioned side view of a disinfecting device in accordance with a representative embodiment of the present invention.

Referring now to FIGS. 3A and 3B, a gravity feed disinfecting device 300 is shown. In some embodiments, security bins 390 are passively moved through interior 312 of disinfecting device 300 by gravity, wherein upstream opening 320 is positioned at a height that is greater than a height of downstream opening or exit 330. In some embodiments, upstream opening 320 is coupled to downstream opening through interior 312 via a passive conveyor 354, such as a gravity roller conveyor, wherein at least a portion of passive conveyor 354 is transparent or translucent to permit passage of antimicrobial wavelengths emitted from light source(s) 370 during an active state of device 300. In some embodiments, an angle 375 of passive conveyor 354 is selected to achieve a desired speed at which security bin 390 passes through interior 312. In some embodiments, passive conveyor 354 is positioned within interior 312 at an angle 375 configured to achieve a desired duration of time over which security bin 390 passes through interior 312. In some instances, a coefficient of friction is selected for passive conveyor which is selected to achieve at least one of a desired speed at which security bin 390 passes through interior 312 and/or a desired duration of time over which security bin 390 passes through interior 312.

In some embodiments, a desired speed at which security bin 390 passes through interior 312 is approximately 60 inches/second, approximately 55 inches/second, approximately 50 inches/second, approximately 48 inches/second, approximately 45 inches/second, approximately 40 inches/second, approximately 36 inches/second, approximately 30 inches/second, approximately 28 inches/second, approximately 24 inches/second, approximately 20 inches/second, approximately 18 inches/second, approximately 12 inches/second, approximately 8 inches/second, approximately 6 inches/second, approximately 1 inch/second, or less than 1 inch/second.

In some embodiments, a desired duration of time over which security bin 390 passes through interior 312 is less than one second, approximately less than one second, approximately 1 second, approximately 1.5 second, approximately 2 seconds, approximately 2.5 seconds, approximately 5 seconds, approximately 7.5 seconds, approximately 10 seconds, approximately 15 seconds, approximately 20 seconds, approximately 25 seconds, approximately 30 seconds, less than 30 seconds, or greater than 30 seconds. In some embodiments, a desired duration of time over which security bin 390 passes through interior 312 is one second. In some embodiments, a desired duration of time over which security bin 390 passes through interior 312 is 30 seconds. In some embodiments, a desired duration of time over which security bin 390 passes through interior 312 is less than 30 seconds.

In some embodiments, passive conveyor is positioned within interior 312 at an angle 375 of at least about 20°, at least about 25°, at least about 30°, at least about 35°, at least about 40°, and at least about 45°. In some embodiments, passive conveyor 354 is positioned within interior 312 at an angle of 45°. In some embodiments, passive conveyor 354 is positioned within interior 312 at an angle 375 greater than 45°.

In some embodiments, passive conveyor 354 comprises a coefficient of friction of from approximately 0.1 to approximately 1.0, from approximately 0.15 to approximately 0.95, from approximately 0.2 to approximately 0.9, from approximately 0.25 to approximately 0.85, from approximately 0.3 to approximately 0.8, from approximately 0.35 to approximately 0.8, from approximately 0.4 to approximately 0.75, from approximately 0.45 to approximately 0.7, from approximately 0.5 to approximately 0.65, or from approximately 0.55 to approximately 0.6. In some embodiments, passive conveyor has a coefficient of friction of from approximately 0.2 to approximately 0.35. In some embodiments, passive conveyor 354 comprises a coefficient of friction of from approximately 0.4 to approximately 0.5. In some embodiments, passive conveyor 354 comprises a coefficient of friction of approximately 0.5. In some embodiments, passive conveyor 354 comprises a coefficient of friction of approximately 0.3.

In some embodiments, passive conveyor 354 is a gravity roller conveyor comprising spaces or gaps 362 between adjacent rollers, wherein gaps 362 permit passage of antimicrobial wavelengths from a light source 370 located beneath conveyor 354. In some embodiments, passive conveyor 354 comprises a solid surface that is transparent or translucent to antimicrobial wavelengths emitted from light source 370, such as, for example, a piece of glass, an optically clear polymer sheet, quartz, a Fresnel lens, and the like. In some embodiments, one or more rollers of a gravity roller conveyor comprise an optically clear or optically transparent material configured to permit passage on an antimicrobial wavelength emitted from light source 370.

In some embodiments, conveyor 354 comprises a solid material having a plurality of openings through which may pass an antimicrobial wavelength emitted from light source 370. For example, in some embodiments conveyor 354 comprises a wire mesh or grid. In some embodiments, conveyor 354 comprises a sheet of solid, non-transparent material in which is provided an array or holes or openings. In some embodiments, the sheet of solid, non-transparent material is a metallic material. In some embodiments, the sheet of solid, non-transparent material is a polymer material.

Disinfecting device 300 may comprise any feature disclosed herein. For example, in some embodiments disinfecting device comprises one or more reflectors 380 or 382, a ventilation system comprising a cooling fan 376 and an air filter 377, one or more sensors, such as a laser sensor 384 and a detector or secondary sensor 385 positioned opposite therefrom, an upstream covering 324, and a downstream covering 326. In some embodiments, disinfecting device is used in combination with an inbound conveyor 350 and an outbound conveyor 352. In some embodiments, outbound conveyor 352 comprises a static surface on which security bins 390 collect after exiting housing 310 via downstream opening 330. In some embodiments, outbound conveyor 352 comprises an automated system configured to transport sterilized and/or disinfected security bins 390 to a starting position of a security screening system.

Referring now to FIGS. 4A-4G, a disinfecting device 400 is shown. In some embodiments, device 400 is configured for use with an inbound conveyor 450 coupled to or placed in proximity to upstream opening 420, and further comprises a downstream opening 430 comprising a light shielding hood 432. A bottom lip or rim 433 of hood 432 is positioned below a security bin support surface 460 such that hood 432 shields users from light emitted by light sources 470. In some embodiments, hood 432 and/or rim 433 further comprise a light shielding material or barrier configured to further prevent exposure to light emitted by light sources 470.

Light sources 470 may comprise any light source disclosed herein. In some embodiments, light sources 470 are housed in light housings 472 at upper and lower positions, as shown. The upper and lower positions of light housings 472 are selected at close proximity to upper and lower surfaces of security bins 490 when resting on support surface 460. In some embodiments, light housings 472 and their respective light sources 470 are positioned less than 5 inches, less than 4 inches, less than 3 inches, less than 2 inches, or less than 1 inch from upper and lower surfaces of security bins 490. In some embodiments, upper and lower light housings 472 are positioned opposite one another, wherein the upper light housing is configured to treat the upper and inner surfaces of security bins 490, and wherein the lower light housing is configured to treat the bottom and outer surfaces of security bins 490. In some embodiments, the lower light housing is positioned at the end of support surface 460 such that light source 470 of lower light housing 472 is unobstructed by support surface 460. In some embodiments, support surface 460 comprises an opening into which lower light housing is inserted or otherwise positioned. In some embodiments, at least some portion of support surface 460 is optically clear such that light emitted from lower light source 470 may pass through at least a portion of support surface 460.

Support surface 460 comprises a proximal surface located between upstream opening 420 and light sources 470, and further comprises a distal surface located between light sources 470 and downstream opening 430. In some embodiments, at least one of the proximal surface and the distal surface comprises a plurality of rollers comprising a roller conveyor. In some instances, the proximal surface comprises a solid surface, and the distal surface comprises a roller conveyor. In some embodiments, a central axle of each roller of the roller conveyor is positioned within a pair of oppositely positioned vertical slots, each slot having a depth sufficient to position an upper apex of each roller surface at a height that is in the same plane as the proximal surface. As such, security bin 490 may pass through housing interior 412 in a constant horizontal plane. In some instances, each roller simply drops down into the slots and is retained by gravitational force. In some instances, the axle of each roller is coupled to the slots via a mechanical connection or fastener.

Figure 4A:
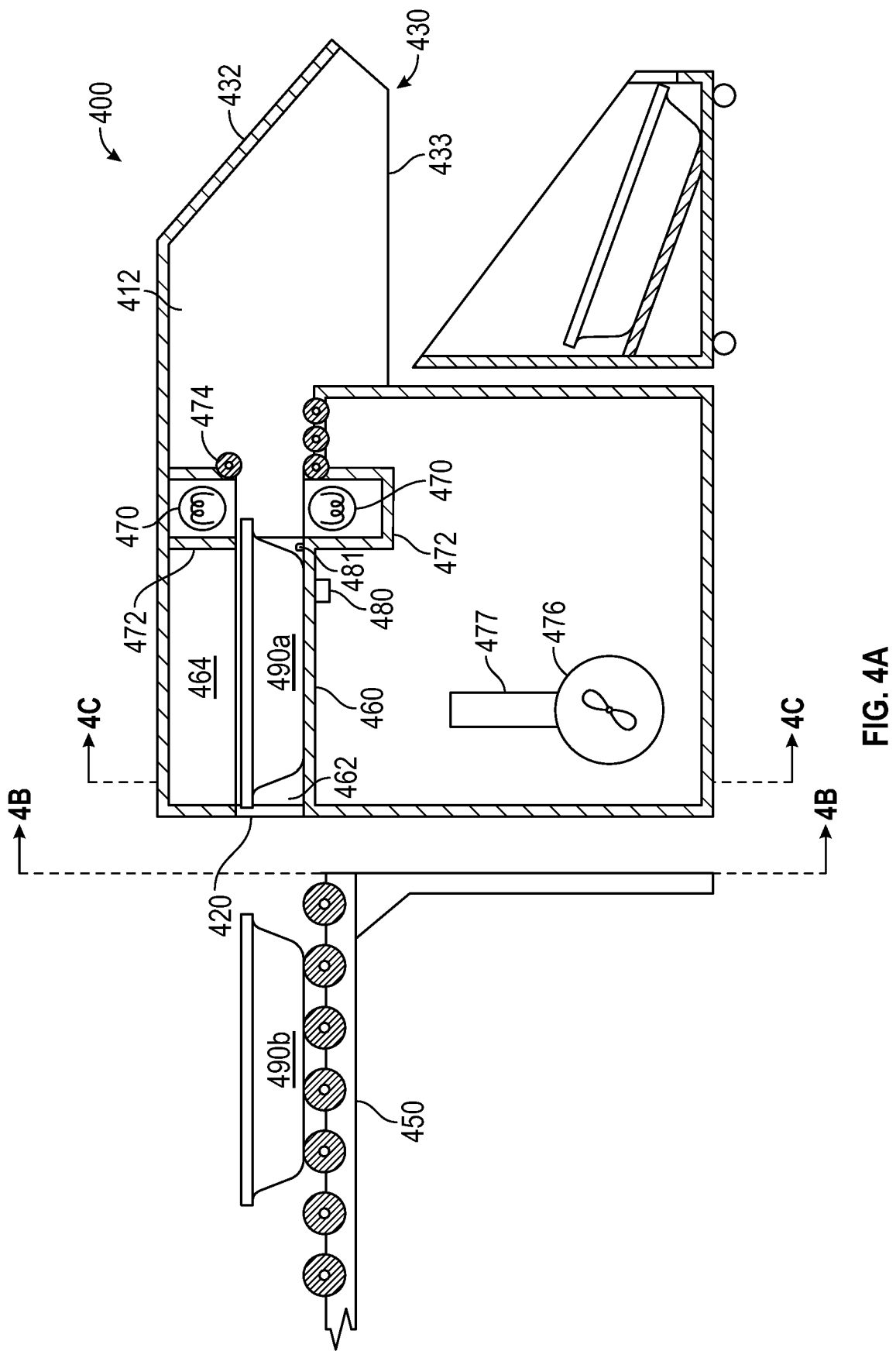
FIG. 4A is a cross-sectioned side view of a disinfecting device having a security bin at a "dead" position in accordance with a representative embodiment of the present invention.
Figure 4B:
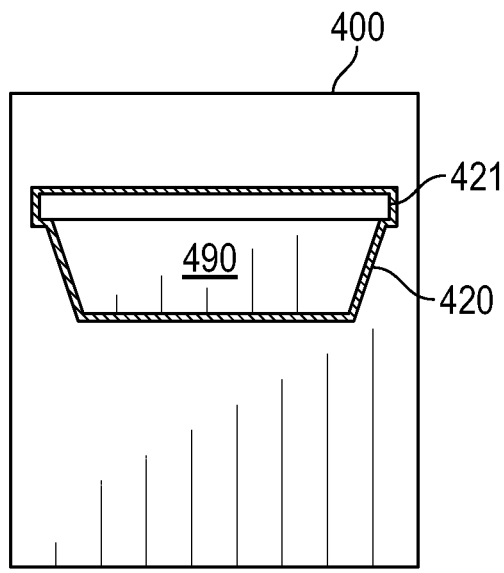
FIG. 4B is a perspective end view of a disinfecting device in accordance with a representative embodiment of the present invention.

In some embodiments, upstream opening 420 comprises a shape that mirrors a cross-sectional shape of security bin 490, as shown in FIG. 4B. Upstream opening 420 is sized to provide a small gap 421 between opening 420 and the outer surface of security bin 490, wherein gap 421 is selected to minimize light leakage between opening 420 and security bin 490. In some instances, gap 421 is less than 10 mm, less than 8 mm, less than 6 mm, less than 5 mm, or less than 2 mm. In some embodiments, a lower surface of upstream opening 420 comprises a proximal-most end of support surface 460, such that a gap is not present between upstream opening 420 and the bottom surface of security bin 490.

Figure 4C:
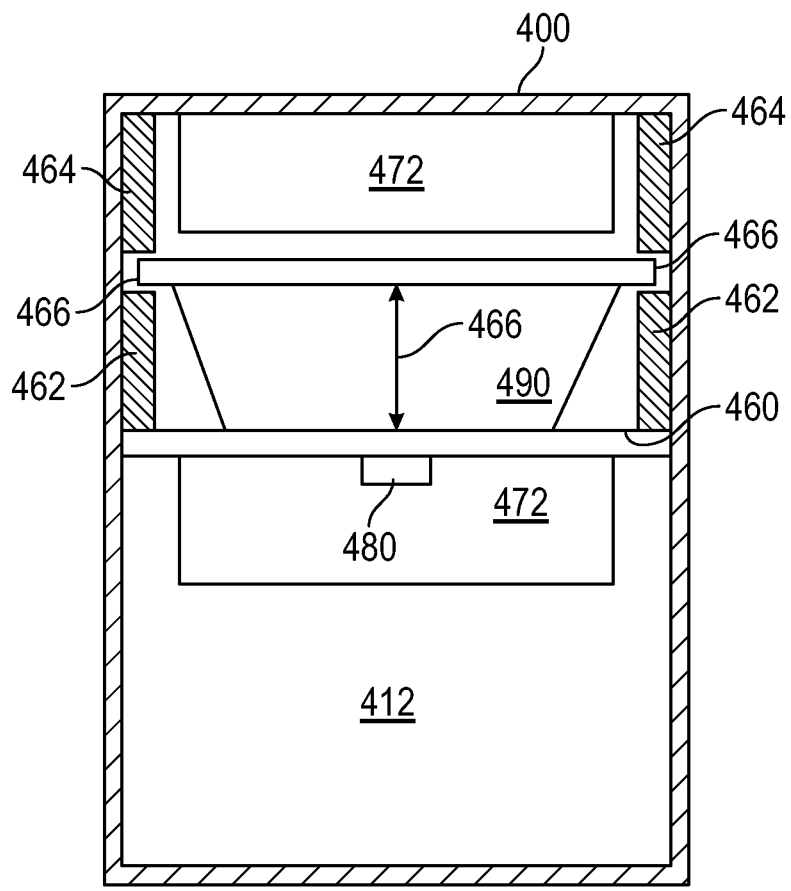
FIG. 4C is a cross-sectioned end view of a disinfecting device in accordance with a representative embodiment of the present invention.

Referring now to FIG. 4C, the proximal surface of support surface 460 further comprises lower lateral guides 462 having a height that is approximately equal, or equal to a height 466 of a lower rim surface of security bin 490. Lower lateral guides 462 are further positioned in proximity to and beneath the lower rim surface of security bin 490. In some instances, the lower rim surface of security bin 490 rest on lower lateral guides 462 as security bin 490 passes through housing interior 412. Lower lateral guides 462 prevent security bin 490 from yawing, or twisting about a vertical axis of security bin 490 as it passes through housing interior 412. In some embodiments, device 400 further comprises upper lateral guides 464 positioned above lower lateral guides 462 and in proximity to upper rim surface of security bin 490. In some instances, a space between upper and lower lateral guides provides a channel 466 configured to receive the rim 492 of security bin 490. Upper lateral guides 464 prevent upward movement of security bin 490, wherein upper lateral guides assist in maintaining contact between support surface 460 and the bottom surface of security bin 490.

In some embodiments, disinfecting device 400 further comprises a bumper 474 positioned in proximity to downstream opening 430 and in proximity to upper light housing 472, wherein bumper 474 is configured to prevent contact between security bin 490 and upper light source 470 as a forward portion of security bin 490 is no longer supported by the distal surface of support surface 460 as security bin 490 exits downstream opening 430, as shown in FIG. 4F. Bumper 474 is generally positioned in close proximity to the upper rim surface of security bin 490. In some embodiments, bumper 474 comprises a roller conveyor. In some embodiments, bumper 474 comprises a wheel.

With continued reference to FIGS. 4A-4G, disinfecting device 400 further comprises a cooling fan 476 and associated ducting 477 sufficient to exhaust heat from housing interior 412. In some instances, ducting 477 is integrated into one or more sidewalls of the enclosure defining housing interior 412, such as, for example, wherein a sidewall of the enclosure is hollow and exhaust from cooling fan 476 is directed into the hollow sidewall. In some embodiments, ducting 477 is operably connected to light housings 472. In some embodiments, cooling fan 476 and/or ducting 477 is further coupled to an external exhaust duct or venting system.

Disinfecting device 400 further comprises a switch 480 having a trigger 481 positioned on or in proximity to support surface 460 at a location in proximity to light housings 472 and/or light sources 470. Trigger 481 is positioned so as to be contacted by the forward or leading bottom edge of security bin 490, as opposed to the rim surfaces of security bin 490. One having ordinary skill in the art will appreciate that other surfaces of security bin 490 may be used in some embodiments to successfully actuate trigger 481 in accordance with the present invention. Trigger 481 is further positioned such that at least a portion of security bin 490 is positioned under light sources 470 when security bin 490 actuates trigger 481. Switch 480 may comprise any type of switch compatible with the present invention. Switch 480 may additionally or alternatively comprise a light curtain, a laser, a mechanical switch, an electrical switch, a motion detector, a heat sensor, or any other suitable component or technology compatible with the present invention. In one representative embodiment, switch 480 comprises an electrical switch operably connected with light sources 470, wherein when trigger 481 is contacted by the bottom leading or forward edge of security bin 490, light sources 470 are activated and emit light onto security bin 490. In some embodiments, actuation of trigger 481 activates light sources 470 to emit a preprogrammed pattern or operation of light emission (i.e., 6 pulses/sec for a total of 3 seconds), regardless of the duration for which trigger 481 is maintained in an actuated position. In some embodiments, actuation of trigger 481 activates light sources 470 to emit light onto security bin 490 until trigger 481 is no longer actuated. In some embodiments, actuation of trigger 481 further starts a timer defining a minimum time between allowed actuations of trigger 481. In some instances, a minimum time between allowed actuations of trigger 481 is less than 10 seconds, less than 6 seconds, less than 5 seconds, less than 4 seconds, less than 3 seconds, less than 2 seconds, or less than 1 second.

Figure 4D:
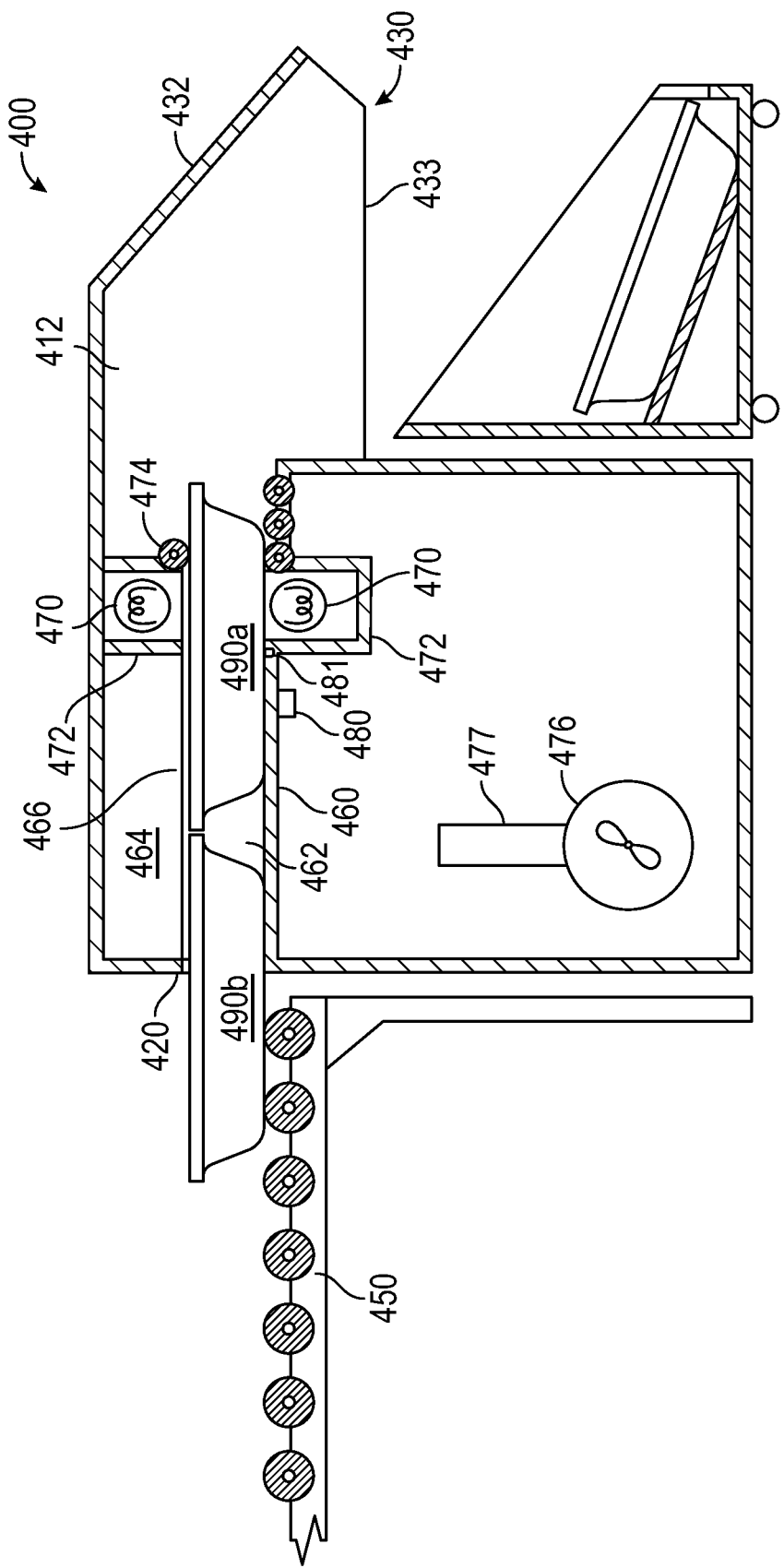
FIG. 4D is a cross-sectioned side view of a disinfecting device having a first security bin at an "active" position and a second security bin partially at a "dead" position in accordance with a representative embodiment of the present invention.

With continued reference to FIGS. 4A-4G, disinfecting device 400 is configured to receive security bins 490 at upstream opening 420, wherein the proximal surface of support surface 460 is configured to have a length that is approximately equal to the length of security bin 490. The profile shape of upstream opening 420, and the close tolerance of gap 421 prevent security bin 490a from being directly inserted into device 400 at a depth sufficient to actuate trigger 481. Instead, security bin 490a is only capable of being directly inserted into a "dead" position on the proximal surface of support surface 460, as shown in FIG. 4A. The "dead" position of security bin 490a is at least characterized by i) a portion of security bin 490a being located on proximal surface of support surface 460, ii) a portion of security bin 490a being positioned within upstream opening 420, and iii) the forward or leading bottom edge of security bin 490a being positioned in close proximity to trigger 481, but not in contact with trigger 481. Security bin 490a remains in this "dead" position until security bin 490a is further advanced towards downstream opening 430 by insertion of a second security bin 490b into upstream opening 420, as shown in FIG. 4D.

With continued reference to FIG. 4D, upon insertion of a second security bin 490b into upstream opening 420, the rim of second security bin 490b contacts the rim of security bin 490a to advance the position of security bin 490a out of the "dead" position and into an "active" position. The "active" position of security bin 490a is at least characterized by i) actuation of trigger 481 by security bin 490a, ii) light sources 470 emitting light onto security bin 490a, iii) a portion of second security bin 490b being positioned within upstream opening 420, and iv) a portion of second security bin 490a being located in the "dead" position. The action of inserting second security bin 490b into the "dead" position and concomitantly advancing security bin 490a into the "active" position causes security bin 490a to simultaneously actuate trigger 481 and advance across light sources 470 while light sources 470 are emitting antimicrobial light. The "dead" position of second security bin 490b substantially prevents light leakage from upstream opening 420 while security bin 490a is in the "active" position.

Figure 4E:
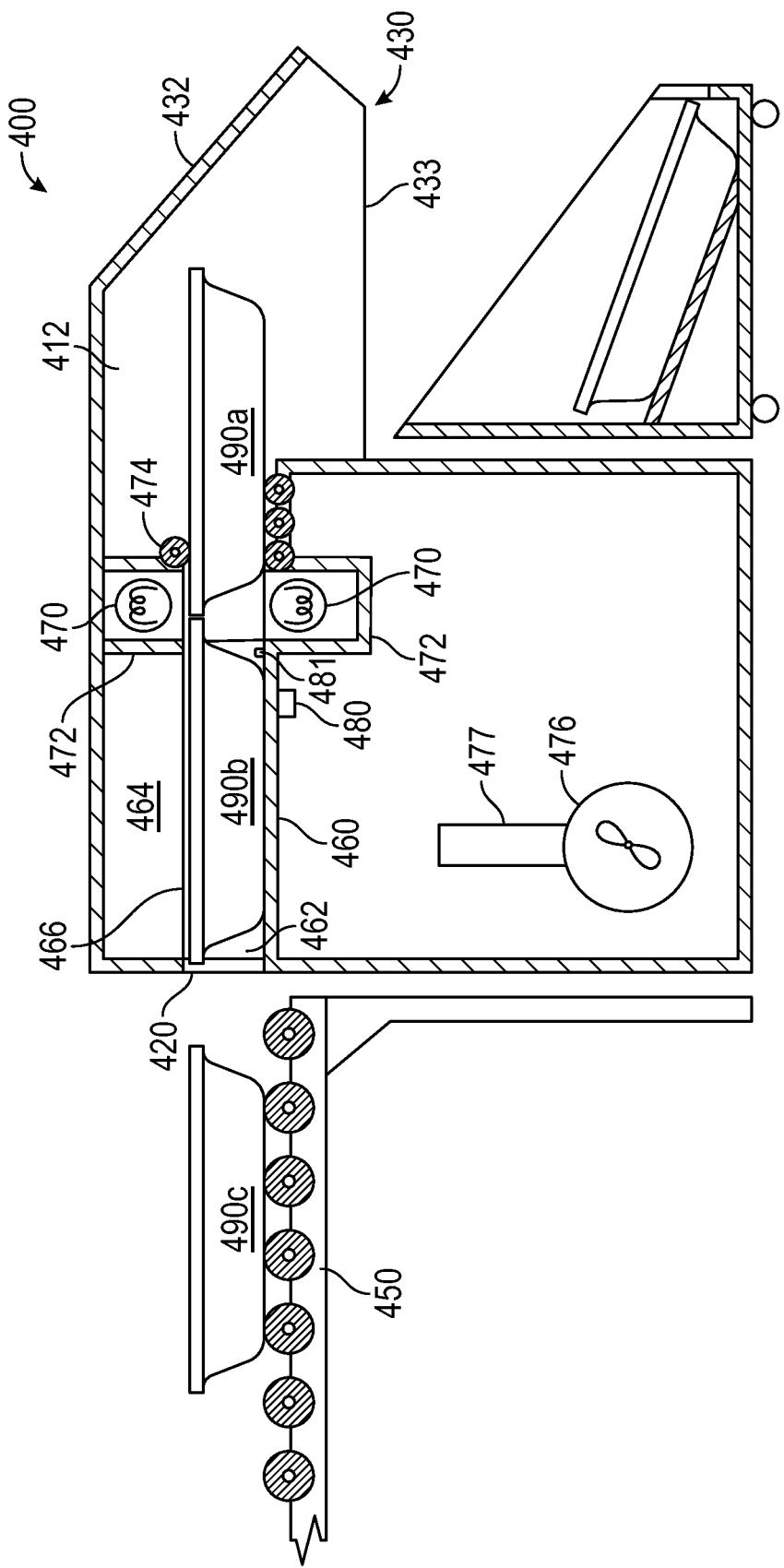
FIG. 4E is a cross-sectioned side view of a disinfecting device having a first security bin at an "active" position and a second security bin at a "dead" position in accordance with a representative embodiment of the present invention.
Figure 4G:
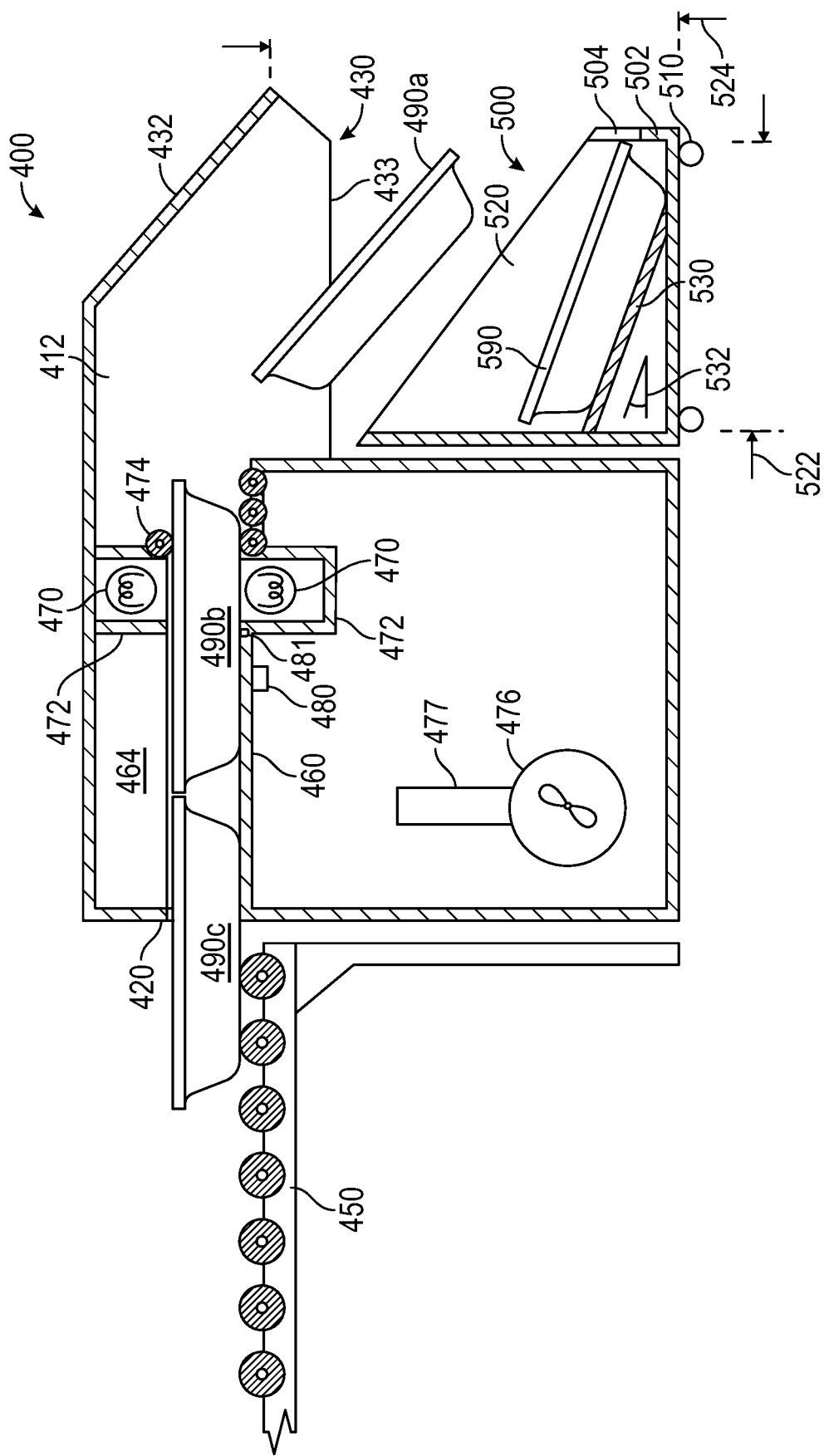
FIG. 4G is a cross-sectioned side view of a disinfecting device having a first security bin shown in freefall, a second security bin at an "active" position, and a third security bin partially at a "dead" position in accordance with a representative embodiment of the present invention.

When second security bin 490b is fully inserted into the "dead" position, a portion of security bin 490a is positioned on the distal surface of support surface 460, as shown in FIG. 4E. Upon insertion of a third security bin 490c into upstream opening 420, the rim of third security bin 490c contacts the rim of second security bin 490b to advance the position of second security bin 490b out of the "dead" position and into the "active" position, while simultaneously advancing security bin 490 towards downstream opening 430, as shown in FIG. 4F. As security bin 490 is further advanced towards downstream opening 430, a substantial portion of security bin 490 extends beyond the distal surface of support surface 460. At the point where less than half of the bottom surface of security bin 490 is in contact with support surface 460, bumper 474 contacts the upper rim of security bin 490 to prevent contact between security bin 490 and upper light source 470, whereby security bin 490 is momentarily held in a cantilevered position, as shown. Upon further advancement of third security bin 490c into the "dead" position and second security bin 490b into the "active" position, security bin 490 loses contact with bumper 477 and exits device 400 via downstream opening 430, as shown in FIG. 4G.

In some embodiments, disinfecting device 400 further comprises a cart 500 for collecting treated security bins 590. Cart 500 comprises an opening 520 having a length 522 that is less than a length of security bin 590. Cart 500 further comprises a floor 530 set at an angle 532 of approximately 30°. A front edge 502 of cart 500 comprises a height that is greater than a height of security bin 590. Front edge 502 further comprises a cutout 504 to provide access to security bins located below the height of front edge 502. In some embodiments, cart 500 further comprises wheels 510 (i.e., caster wheels) for mobility.

A height 524 between floor 530 and support surface 460 is selected to facilitate accurate and repeatable stacking of security bins 590 upon exit from downstream opening 430. In at least some preferred embodiments, security bins 590 are permitted to freefall from the distal surface of support surface 460 and into cart 500, wherein height 524 and angle 532 are selected facilitate stacking of treated security bins 590. In some embodiments, height 524 is less than or equal to 36 inches, less than or equal to 42 inches, less than or equal to 48 inches, or less than or equal to 54 inches. In some embodiments, angle 532 is approximately 15°, approximately 20°, approximately 25°, approximately 27°, approximately 30°, approximately 32°, approximately 35°, approximately 40 degrees, approximately 42°, or approximately 45°.

In some embodiments, the present invention provides a disinfecting device comprising an automated system utilizing a preprogrammed protocol, motors, controllers, sensors, conveyors, and software for controlling the same, wherein the automated system is designed to move a security bin through the disinfecting device according to one or more embodiments described herein. In some embodiments, an automated system of the present invention comprises an automated door that opens to accept a security bin into the housing interior, and closes prior to activating the light source of the device, such that the door prevents undesired external exposure to the light source. In some embodiments, an automated system of the present invention actively moves a security bin through the housing interior at a speed to ensure sufficient exposure to the antimicrobial wavelength in order to achieve a desired level of disinfection for the security bin.

In some embodiments, an automated system of the present invention further comprises a system for detecting the presence of microbial cells, wherein the detection system automatically varies the exposure time of the security bin to the antimicrobial wavelength based on data gathered by the detection system; for example, the automated system may decrease the speed at which the security bin passes through the disinfecting device, and/or may increase the intensity or number of light pulses during the exposure time. In some embodiments, a detection system comprises a UV light source and a charge coupled device (CCD) sensor or camera capable of detecting fluorescence emitted by microbial cells when exposed to UV light. The detection system may further include a set of parameters that the automated system references to determine and set a custom exposure time based on the data obtained from each security bin. In some embodiments, the detection system comprises one or more additional sensors configured to detect non-microbial substances, such as, for example, gunpowder or explosives residue, narcotics, or body fluids.

The present invention further comprises a method for disinfecting a container, including but not limited to a security bin. In some embodiments, a method of disinfecting a surface of a security bin comprising steps for providing a disinfecting device of the present invention; introducing the security bin to an interior of the disinfecting device via an upstream opening of the disinfecting device; emitting an antimicrobial wavelength onto the surface of the security bin; and retrieving the security bin from the interior of the device via the downstream opening of the device. In some embodiments, a method of the invention further comprises a step for cumulatively disinfecting the surface of the security bin by repeatedly introducing the security bin in the interior of the device and emitting an antimicrobial wavelength onto the surface of the security bin.

EXAMPLES

Airport Security Bin Treatment

A disinfecting device of the present invention was used to disinfect three airport security bins. The disinfecting device comprised a pulsed gas discharge lamp configured to emit an anti-microbial wavelength of 240 nm. The disinfecting device further comprised a controller configured to emit the antimicrobial wavelength for a desired length of exposure time, at a pulse rate of 6 pulses/second, and at an energy of 505 joules/pulse. Further, the disinfecting device comprised means for moving the airport security bins through the disinfecting device at a rate/speed sufficient to achieve a desired length of exposure time.

Sterile LB agar plates were prepared according to well-known scientific techniques and procedures. A control plate was provided. Triplicate sample plates were provided for each tested surface, of each security bin, for each exposure time (at total of 91 sample plates).

Cotton swabs were used to collect samples from outside and inside surfaces of each security bin following exposure time to the antimicrobial wavelength of 0 seconds, 2 seconds, 5 seconds, and 10 seconds. The samples were applied to the agar plates and incubated at 37° Celsius overnight. The agar plates were collected and visually analyzed. The results of the test are provided in Table 1, wherein the percentage represents the surface area of the agar plate comprising bacterial colonies.

TABLE 1

|  | O/N incubation | 0 secs exp | 2 secs exp | 5 secs exp | 10 secs exp |
| --- | --- | --- | --- | --- | --- |
| Control | 0% | 0% | N/A | N/A | N/A |
| Bin 1 inside | 100% | 100% | <5% | 0% | 0% |
| Bin 1 (outside) | 100% | 100% | <5% | 0% | 0% |
| Bin 2 (inside) | 100% | 100% | <5% | 0% | 0% |
| Bin 2 (outside) | 100% | 100% | <1% | 0% | 0% |
| Bin 3 (inside) | 100% | 100% | <1% | 0% | 0% |
| Bin 3 (outside) | 100% | 100% | <1% | 0% | 0% |

As shown in Table 1, all unexposed samples produced 100% bacterial coverage following the overnight incubation. Conversely, all bacteria was eliminated after 5 seconds of exposure time to the antimicrobial wavelength, and a significant reduction in bacteria was achieved after 2 seconds of exposure time.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description.

What is claimed is:

1. A device for disinfecting a container, said device comprising:

a housing having an upstream opening, a downstream opening, and an interior, said upstream opening comprising a horizontal top having a first width, a horizontal bottom having a second width that is less than the first width, a tapered left side extending outwardly from the horizontal bottom, a tapered right side extending outwardly from the horizontal bottom, a vertical left side extending downwardly from the horizontal top and coupled to the tapered left side to form a left channel, and a vertical right side extending downwardly from the horizontal top and coupled to the tapered right side to form a right channel;

a pathway extending between the upstream opening and the downstream opening, said pathway comprising an upper lateral guide, a lower lateral guide, and a lateral channel interposed therebetween, said lateral channel in alignment with at least one of the left channel and the right channel of the upstream opening, said pathway further comprising a support surface having a length that is approximately equal to a length of a container; and a light source positioned within the housing and in proximity to the pathway, said support surface being interposed between the light source and the upstream opening, wherein the light source is configured to emit an antimicrobial wavelength.

2. The device of claim 1, wherein the light source is a pulsed gas discharge lamp.

3. The device of claim 1, wherein the light source is a UV lamp.

4. The device of claim 1, further comprising a first covering coupled to the upstream opening and a second covering coupled to the downstream opening, wherein said first and second coverings each comprise a closed position and an open position.

5. The device of claim 4, wherein at least one of the first and second coverings is a brush seal.

6. The device of claim 4, wherein the open position of the first covering permits passage of a container into the interior, and wherein the closed position of the first covering substantially retains within the interior the antimicrobial wavelength emitted from the light source.

7. The device of claim 4, wherein the open position of the second covering permits a container to exit the interior, and wherein the closed position of the second covering substantially retains within the interior the antimicrobial wavelength emitted from the light source.

8. The device of claim 1, wherein the pathway comprises a conveyor.

9. The device of claim 8, wherein the conveyor is at least partially transparent to the antimicrobial wavelength emitted from the light source.

10. The device of claim 8, wherein the conveyor is a passive conveyor.

11. The device of claim 10, wherein the passive conveyor is a gravity roller conveyor.

12. The device of claim 10, wherein the passive conveyor is a solid surface comprising at least one of a translucent material, a transparent material, and an optically clear material.

13. The device of claim 10, wherein the passive conveyor is a solid surface having a plurality of openings through which the antimicrobial wavelength passes.

14. The device of claim 13, wherein the passive conveyor is a wire mesh.

15. The device of claim 8, wherein the conveyor is a motor-driven conveyor.

16. The device of claim 1, further comprising at least one of an inbound conveyor coupled to the upstream opening, and an outbound conveyor coupled to the downstream opening.

17. The device of claim 16, wherein the inbound conveyor or the outbound conveyor are components of a security screening system.

18. The device of claim 1, wherein the container is a security bin.

* * * * *